US012635990B2

(12) United States Patent
Iwasaki et al.

(10) Patent No.: US 12,635,990 B2
(45) Date of Patent: May 26, 2026

(54) ULTRASOUND DIAGNOSIS APPARATUS AND ULTRASOUND SIGNAL GENERATION METHOD

(71) Applicant: CANON MEDICAL SYSTEMS CORPORATION, Tochigi (JP)

(72) Inventors: Ryosuke Iwasaki, Otawara (JP); Hiroki Takahashi, Nasushiobara (JP); Tomohisa Imamura, Otawara (JP); Ting Xia, Vernon Hills, IL (US); Liang Cai, Vernon Hills, IL (US); Jian Zhou, Vernon Hills, IL (US)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 265 days.

(21) Appl. No.: 18/329,070

(22) Filed: Jun. 5, 2023

(65) Prior Publication Data

US 2024/0398386 A1    Dec. 5, 2024

(51) Int. Cl.
| | |
|---|---|
| *A61B 8/00* | (2006.01) |
| *G01S 7/52* | (2006.01) |
| *G01S 15/89* | (2006.01) |

(52) U.S. Cl.
CPC ........ *A61B 8/5269* (2013.01); *G01S 7/52077* (2013.01); *G01S 15/8977* (2013.01)

(58) Field of Classification Search
None
See application file for complete search history.

(56) References Cited

U.S. PATENT DOCUMENTS

| | | | |
|---|---|---|---|
| 11,564,659 B2 | 1/2023 | Yoshiara et al. | |
| 2002/0165451 A1* | 11/2002 | Phelps | G01S 15/8977 |
| | | | 600/437 |
| 2009/0216124 A1* | 8/2009 | Chono | G01S 7/52087 |
| | | | 600/443 |
| 2016/0045185 A1* | 2/2016 | Nakatsuka | A61B 8/4416 |
| | | | 600/443 |
| 2016/0166237 A1* | 6/2016 | Yoshiara | G01S 7/52039 |
| | | | 600/443 |
| 2017/0071569 A1* | 3/2017 | Sato | G01S 7/52033 |
| 2019/0094357 A1* | 3/2019 | Freeman | G01S 7/52026 |
| 2021/0275147 A1* | 9/2021 | Ota | A61B 8/565 |
| 2022/0206130 A1* | 6/2022 | Li | G06N 3/047 |

FOREIGN PATENT DOCUMENTS

| | | |
|---|---|---|
| JP | 2016-112400 A | 6/2016 |
| JP | 2017-55845 A | 3/2017 |

* cited by examiner

*Primary Examiner* — Patricia J Park
(74) *Attorney, Agent, or Firm* — Oblon, McClelland, Maier & Neustadt, L.L.P.

(57) ABSTRACT

An ultrasound diagnosis apparatus of an embodiment includes storage circuitry and processing circuitry. The storage circuitry stores therein a trained model trained using a first ultrasound signal containing a saturated signal as input data and a second ultrasound signal in which effect of saturation is reduced from the first ultrasound signal, as target data. The processing circuitry inputs a third ultrasound signal containing a saturated signal to the trained model and acquires a fourth ultrasound signal that is output from the trained model and in which effect of saturation is reduced from the third ultrasound signal, to generate the fourth ultrasound signal.

14 Claims, 17 Drawing Sheets

FIG.3

~AT TIME OF TRAINING~

~AT TIME OF INFERENCE~

FIG.11

~AT TIME OF INFERENCE~

~AT TIME OF TRAINING~

~AT TIME OF INFERENCE~

~AT TIME OF TRAINING~

~AT TIME OF INFERENCE~

~AT TIME OF TRAINING~

~AT TIME OF INFERENCE~

ULTRASOUND DIAGNOSIS APPARATUS AND ULTRASOUND SIGNAL GENERATION METHOD

FIELD

Embodiments described herein relate generally to ultrasound diagnosis apparatuses and ultrasound signal generation methods.

BACKGROUND

To acquire ultrasound image data having fewer artifacts, tissue harmonic imaging (THI) using a harmonic component (nonlinear signal) produced in the process of ultrasound propagation is widely used. The second harmonic component is typically used; however, the application of the third harmonic component has also been proposed. Note that an Nth (N is an integer of 2 or greater) harmonic component is also referred to simply as an Nth component or Nth harmonic.

Analog circuitry of an ultrasound diagnosis apparatus has a limited dynamic range of input. To protect the analog circuitry, if the signal value of an input signal is equal to or greater than a certain magnitude, clamping circuitry works on the input signal to clip the waveform so that the signal value of the input signal is a certain value. This saturates the input signal. Then, an odd-multiple harmonic component is superimposed on the signal. Thus, if visualization is performed with the third harmonic component, the band of visualization and the band of harmonics produced by saturation overlap, resulting in image quality degradation.

A configuration of a prefilter and the like or an algorithm restraining such effect of saturation has also been proposed. Unfortunately, this may cause an increase in the circuitry size, signal processing to be required in an earlier stage, or lacking in robustness.

BRIEF DESCRIPTION OF THE DRAWINGS

FIG. 3 is a diagram illustrating example operation of clamping circuitry according to the first embodiment;

FIG. 11 is a diagram illustrating example input data and target data according to the second embodiment;

DETAILED DESCRIPTION

A problem to be solved by the embodiments disclosed in this specification and the drawings is to acquire an ultrasound signal in which effect of saturation is robustly reduced and degradation in image quality is restrained. However, problems to be solved by the embodiments disclosed in this specification and the drawings are not limited to the aforementioned problem. A problem corresponding to each effect of each configuration indicated by the embodiments described below can also be positioned as another problem.

An ultrasound diagnosis apparatus of an embodiment includes storage circuitry and processing circuitry. The storage circuitry stores therein a trained model trained using a first ultrasound signal containing a saturated signal as input data and a second ultrasound signal in which effect of saturation is reduced from the first ultrasound signal, as target data. The processing circuitry inputs a third ultrasound signal containing a saturated signal to the trained model and acquires a fourth ultrasound signal that is output from the trained model and in which effect of saturation is reduced from the third ultrasound signal, to generate the fourth ultrasound signal.

An ultrasound diagnosis apparatus and an ultrasound signal generation method according to each embodiment and each modification will be described below with reference to the drawings.

First Embodiment

Figure 1:
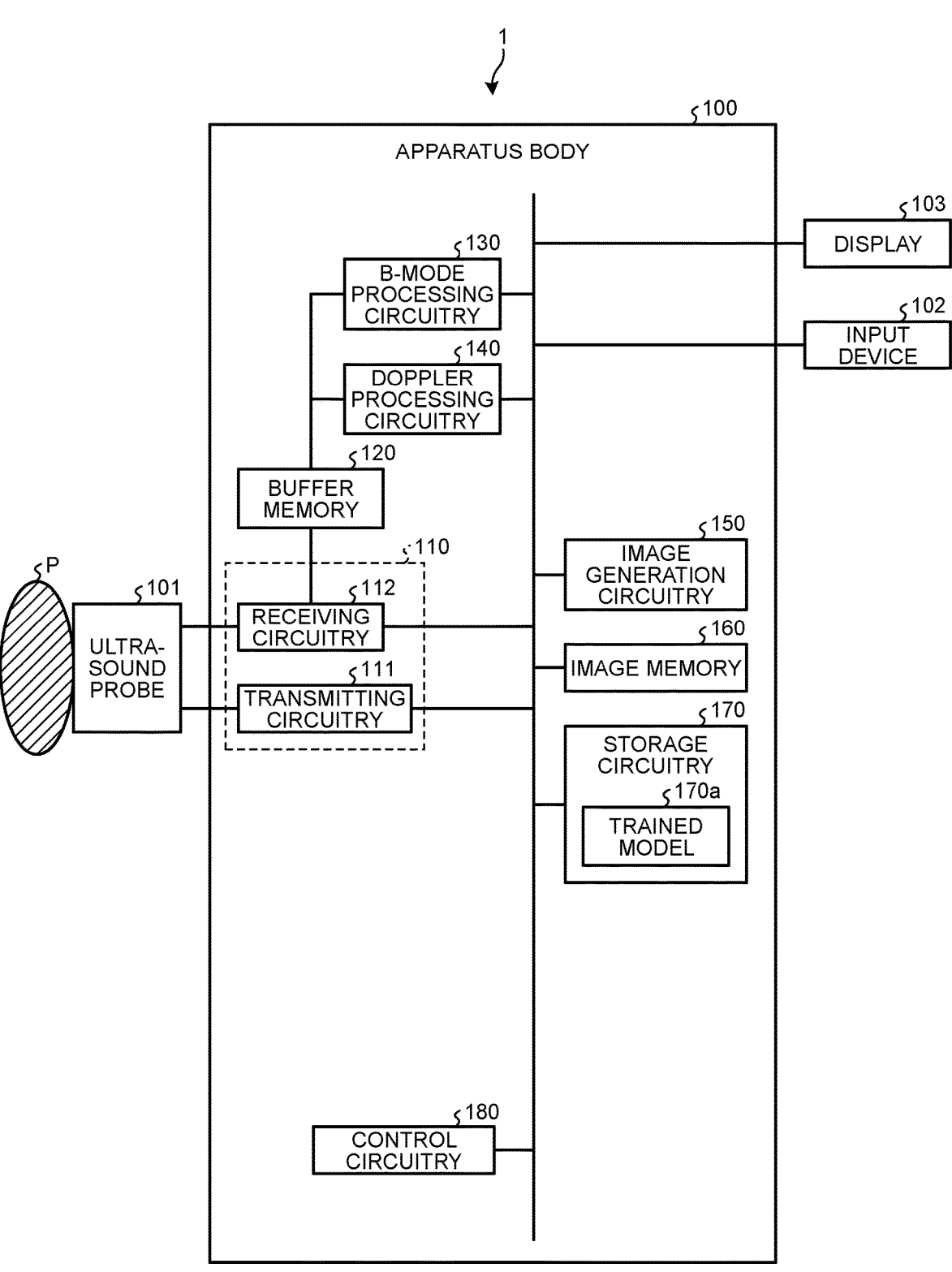
FIG. 1 is a block diagram illustrating an example configuration of an ultrasound diagnosis apparatus according to a first embodiment.

FIG. 1 is a block diagram illustrating an example configuration of an ultrasound diagnosis apparatus 1 according to a first embodiment. As exemplified in FIG. 1, the ultrasound diagnosis apparatus 1 of the first embodiment includes an apparatus body 100, an ultrasound probe 101, an input device 102, and a display 103.

The ultrasound probe 101 includes, for example, a plurality of elements (piezoelectric transducer elements, piezoelectric elements). These elements produce ultrasound on the basis of a driving signal supplied from transmitting circuitry 111 of transmitting/receiving circuitry 110 of the apparatus body 100. In specific, by applying voltage (transmission driving voltage) by the transmitting circuitry 111, the elements produce ultrasound having a waveform in accordance with the transmission driving voltage. The waveform of the transmission driving voltage indicated by the driving signal is the waveform of the voltage applied to the elements. That is, the ultrasound probe 101 transmits ultrasound in accordance with the magnitude of the applied transmission driving voltage. Furthermore, the ultrasound probe 101 receives a reflected wave from a subject P, converts the received reflected wave into a reflected wave signal being an electric signal, and outputs the reflected wave signal to the apparatus body 100. The reflected wave signal is an example ultrasound signal. The ultrasound probe 101 also includes, for example, a matching layer provided on the elements, a backing material preventing backward propagation of ultrasound from the elements, and the like. Note that the ultrasound probe 101 is detachably connected to the apparatus body 100.

When the ultrasound probe 101 transmits ultrasound to the subject P, the transmitted ultrasound is successively reflected off surfaces of discontinuity of acoustic impedance in body tissues of the subject P and is received by the elements of the ultrasound probe 101 as a reflected wave. The amplitude of the received reflected wave depends on the difference in the acoustic impedance at the discontinuity surfaces reflecting the ultrasound. Note that when the transmitted ultrasound pulse is reflected off a surface of a moving object, such as a moving blood flow and a cardiac wall, the reflected wave undergoes frequency shift depending on the velocity component relative to the ultrasound transmitting direction of the moving object because of the Doppler effect. The ultrasound probe 101 then outputs the reflected wave signal to receiving circuitry 112, described later, of the transmitting/receiving circuitry 110.

The ultrasound probe 101 is provided so as to be detachable from the apparatus body 100. When a two-dimensional region in the subject P is scanned (two-dimensional scanning), an operator connects, for example, a 1D array probe, in which a plurality of elements are arranged in one row, to the apparatus body 100 as the ultrasound probe 101. Types of 1D array probe include linear ultrasound probes, convex ultrasound probes, sector ultrasound probes, and the like. When a three-dimensional region in the subject P is scanned (three-dimensional scanning), the operator connects, for example, a mechanical 4D probe or a 2D array probe to the apparatus body 100 as the ultrasound probe 101. The mechanical 4D probe can perform two-dimensional scanning using a plurality of elements arranged in one row like 1D array probes and can also perform three-dimensional scanning by oscillating the elements at a predetermined angle (oscillation angle). The 2D array probe can perform three-dimensional scanning with a plurality of elements arranged in a matrix and can also perform two-dimensional scanning by transmitting ultrasound in a converged manner.

The input device 102 is implemented by input means, such as a mouse, a keyboard, a button, a panel switch, a touch command screen, a foot switch, a trackball, and a joystick. The input device 102 receives various setting requests from the operator of the ultrasound diagnosis apparatus 1 and transfers the received various setting requests to the apparatus body 100.

The display 103 displays, for example, a graphical user interface (GUI) for the operator of the ultrasound diagnosis apparatus 1 to input various setting requests using the input device 102, an ultrasound image based on ultrasound image data generated in the apparatus body 100, and the like. The display 103 is implemented by a liquid crystal monitor, an organic light emitting diode (OLED) monitor, or the like. The display 103 is an example display unit.

The apparatus body 100 generates ultrasound image data on the basis of the reflected wave signal transmitted from the ultrasound probe 101. Note that the ultrasound image data is an example ultrasound signal and is also example image data. The apparatus body 100 can generate two-dimensional ultrasound image data on the basis of the reflected wave signal transmitted from the ultrasound probe 101 and corresponding to a two-dimensional region of the subject P. The apparatus body 100 can also generate three-dimensional ultrasound image data on the basis of the reflected wave signal transmitted from the ultrasound probe 101 and corresponding to a three-dimensional region of the subject P. As illustrated in FIG. 1, the apparatus body 100 includes the transmitting/receiving circuitry 110, a buffer memory 120, B-mode processing circuitry 130, Doppler processing circuitry 140, image generation circuitry 150, an image memory 160, storage circuitry 170, and control circuitry 180.

The transmitting/receiving circuitry 110 causes the ultrasound probe 101 to transmit ultrasound and to receive the reflected wave of the ultrasound under control of the control circuitry 180. That is, the transmitting/receiving circuitry 110 performs scanning through the ultrasound probe 101. Note that scanning is also referred to as ultrasound scanning. The transmitting/receiving circuitry 110 is an example transmitting/receiving unit. The transmitting/receiving circuitry 110 includes the transmitting circuitry 111 and the receiving circuitry 112. The transmitting circuitry 111 is an example transmitting unit, and the receiving circuitry 112 is an example receiving unit.

The transmitting circuitry 111 supplies a driving signal to the ultrasound probe 101 to cause the ultrasound probe 101 to transmit ultrasound under control of the control circuitry 180. The transmitting circuitry 111 includes rate pulser production circuitry, transmission delay circuitry, and a transmission pulser. When a two-dimensional region in the subject P is scanned, the transmitting circuitry 111 causes the ultrasound probe 101 to transmit an ultrasound beam for scanning the two-dimensional region. When a three-dimensional region in the subject P is scanned, the transmitting circuitry 111 causes the ultrasound probe 101 to transmit an ultrasound beam for scanning the three-dimensional region.

The rate pulser production circuitry repeatedly produces a rate pulse for forming transmission ultrasound (transmission beam) at a predetermined pulse repetition frequency (PRF) under control of the control circuitry 180. The rate pulse passes through the transmission delay circuitry, so that voltage is applied to the transmission pulser while having different transmission delay time. For example, the transmission delay circuitry provides, to each rate pulse produced by the rate pulser production circuitry, transmission delay time for each element necessary for determining transmission directivity with the ultrasound produced from the ultrasound probe 101 converged into a beam. The transmission pulser supplies the driving signal (driving pulse) to the ultrasound probe 101 at timing based on the rate pulse. That is, the transmission pulser applies, to the ultrasound probe 101, voltage (transmission driving voltage) of a waveform indicated by the driving signal at the timing based on the rate pulse. Note that the transmission delay circuitry varies the transmission delay time provided to each rate pulse to arbitrarily adjust the transmitting direction of the ultrasound from the element surface.

The driving pulse is transmitted from the transmission pulser via a cable to the elements in the ultrasound probe 101 and is then converted from an electric signal into mechanical oscillation in the elements. That is, voltage application to the elements mechanically oscillates the elements. Ultrasound produced by this mechanical oscillation is transmitted inside a living body (inside the subject P). Here, the ultrasound having the transmission delay time different between the elements is converged and propagates in a predetermined direction.

Note that the transmitting circuitry 111 has a function capable of instantaneously varying the transmission frequency, transmission driving voltage, and the like to execute a predetermined scanning sequence under control of the control circuitry 180. In particular, varying of the transmission driving voltage is implemented by sending circuitry of the linear amplifier type capable of instantaneously switching the value of the transmission driving voltage or a mechanism electrically switching a plurality of power source units. Note that the transmission frequency is, for example, the center frequency of the transmitted ultrasound.

The reflected wave of the ultrasound transmitted by the ultrasound probe 101 reaches the elements in the ultrasound probe 101 and is then converted from the mechanical oscillation into an electrical signal (reflected wave signal), and the reflected wave signal is input to the receiving circuitry 112.

The receiving circuitry 112 performs various types of processing to the reflected wave signal transmitted from the ultrasound probe 101 to generate reflected wave data. The receiving circuitry 112 then stores the generated reflected wave data in the buffer memory 120. Note that the reflected wave data is an example ultrasound signal.

Figure 2:
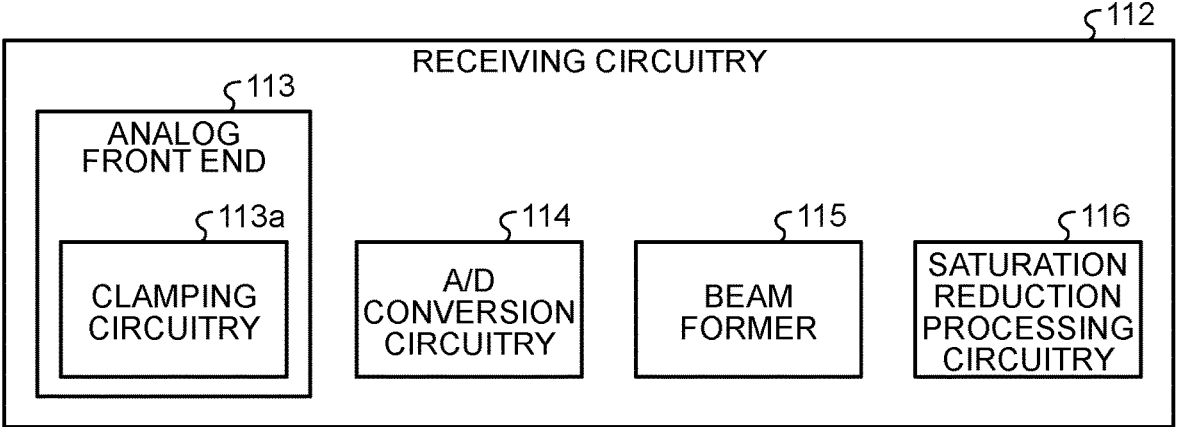
FIG. 2 is a diagram illustrating an example configuration of receiving circuitry according to the first embodiment.

FIG. 2 is a diagram illustrating an example configuration of the receiving circuitry 112 according to the first embodiment. As illustrated in FIG. 2, the receiving circuitry 112 includes an analog front end 113, analog-to-digital (A/D) conversion circuitry (A/D converter) 114, a beam former 115, and saturation reduction processing circuitry 116.

To the analog front end 113, the reflected wave signal is input from the ultrasound probe 101. The analog front end 113 is analog circuitry performing known analog processing (analog signal processing) on the input reflected wave signal and outputting the reflected wave signal being an analog signal subjected to the analog processing to the A/D conversion circuitry 114. For example, to describe a portion of the processing executed by the analog front end 113, the analog front end 113 includes, for example, a preamplifier, and the preamplifier amplifies the reflected wave signal for each channel and performs gain adjustment (gain correction).

Figure 3:
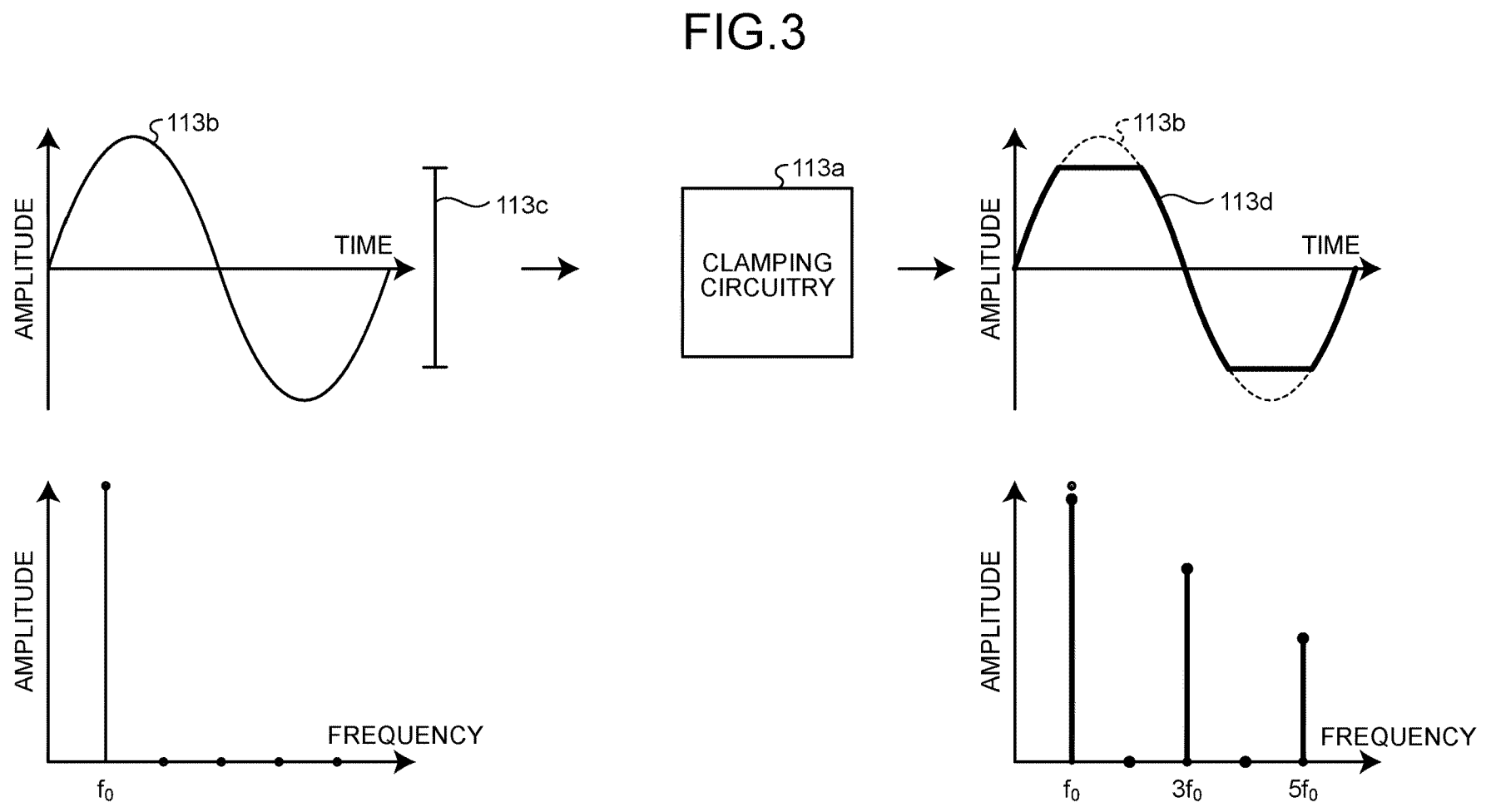

The analog front end 113 also includes clamping circuitry 113$a$. FIG. 3 is a diagram illustrating example operation of the clamping circuitry 113$a$ according to the first embodiment. For example, as illustrated in FIG. 3, the clamping circuitry 113$a$ converts a reflected wave signal 113$b$ into a reflected wave signal 113$d$ so that the amplitude of the reflected wave signal 113$b$ input to the preamplifier falls within a predetermined tolerance range 113$c$ and inputs the reflected wave signal 113$d$ to the preamplifier. For example, the clamping circuitry 113$a$ clips (fixes) the amplitude of the reflected wave signal 113$b$ equal to or greater than a certain value to the certain value to generate the reflected wave signal 113$d$. The clamping circuitry 113$a$ then outputs the reflected wave signal 113$d$ toward the preamplifier. This protects the preamplifier being circuitry in the analog front end 113 from an excessive high-voltage pulse of the reflected wave signal.

In this way, the clamping circuitry 113$a$ executes clamping processing restraining the signal value, equal to or greater than the certain value, of the reflected wave signal 113$b$ acquired by transmitting and receiving ultrasound to and from the subject P, to the certain value. The clamping processing yields the reflected wave signal 113$d$. Such clamping processing is example processing included in the analog processing.

Here, clipping of the amplitude of the reflected wave signal 113$b$ equal to or greater than a certain value to a certain value is equivalent to convolution of a rectangular wave. Thus, an odd-order harmonic component (such as the third harmonic component and the fifth harmonic component) is superimposed on the reflected wave signal 113$d$. That is, let $f_0$ represent the center frequency (frequency of the fundamental) of the reflected wave signal 113$b$, the reflected wave signal 113$d$ contains an odd-order harmonic component (such as the third harmonic component corresponding to a frequency $3f_0$ and the fifth harmonic component corresponding to a frequency $5f_0$).

Thus, if visualization is performed with the third harmonic on the basis of this reflected wave signal 113$d$, the band of visualization and the band of harmonics produced by saturation overlap, resulting in image quality degradation. That is, the reflected wave signal 113$d$ is affected by saturation, so that image quality of ultrasound image data based on the reflected wave signal 113$d$ is degraded. Therefore, the ultrasound diagnosis apparatus 1 of the first embodiment is configured to be capable of generating an ultrasound signal that does not degrade image quality even if visualization is performed with the third harmonic, as described below.

Returning to description of FIG. 2, to the A/D conversion circuitry 114, the reflected wave signal output from the analog front end 113 is input. The A/D conversion circuitry 114 converts the reflected wave signal into a digital signal through A/D conversion of the reflected wave signal and outputs the reflected wave signal converted into the digital signal to the beam former 115.

To the beam former 115, the reflected wave signal output from the A/D conversion circuitry 114 is input. The beam former 115 applies phasing addition processing to the input reflected wave signal. For example, the beam former 115 provides reception delay time necessary for determining reception directivity, to the reflected wave signal being the digital signal. The beam former 115 then performs addition processing to the reflected wave signal provided with the reception delay time. The addition processing of the beam former 115 emphasizes the reflection component from a direction corresponding to the reception directivity of the reflected wave signal.

The beam former 115 then converts the reflected wave signal subjected to the phasing addition processing into an in-phase signal (I signal) and a quadrature-phase signal (Q signal) in the baseband. The beam former 115 then stores the I signal and Q signal (IQ signal) in the buffer memory 120 as reflected wave data. The beam former 115 is implemented by, for example, processing circuitry including a processor.

The saturation reduction processing circuitry 116 is processing circuitry that operates when input data and target data are generated to be used in generation of a trained model 170a at a learning apparatus 200 described later, that is, at the time of training. To the saturation reduction processing circuitry 116, the reflected wave data output from the B-mode processing circuitry 130 via the beam former 115 is input at the time of training. The reflected wave data input to the saturation reduction processing circuitry 116 at this time is signal data containing the third harmonic component described later. The saturation reduction processing circuitry 116 generates reflected wave data in which effect of saturation is reduced in comparison with the input reflected wave data and transmits the generated reflected wave data to the learning apparatus 200, described later, as target data. Processing executed by the saturation reduction processing circuitry 116 will be described in detail later.

Returning to description of FIG. 1, the receiving circuitry 112 generates two-dimensional reflected wave data from a two-dimensional reflected wave signal transmitted from the ultrasound probe 101. The receiving circuitry 112 also generates three-dimensional reflected wave data from a three-dimensional reflected wave signal transmitted from the ultrasound probe 101.

In this embodiment, the ultrasound diagnosis apparatus 1 can perform various types of processing in real time. For example, the ultrasound probe 101 successively transmits reflected wave signals for one frame to the receiving circuitry 112. Each time the receiving circuitry 112 receives the reflected wave signals for one frame transmitted from the ultrasound probe 101, the receiving circuitry 112 generates reflected wave data for one frame from the reflected wave signals for one frame. Each time the receiving circuitry 112 generates the reflected wave data for one frame, the receiving circuitry 112 stores the reflected wave data for one frame in the buffer memory 120.

The buffer memory 120 is a memory that temporarily stores therein the reflected wave data generated by the transmitting/receiving circuitry 110. For example, the buffer memory 120 is configured to be capable of storing therein the reflected wave data for a predetermined number of frames. If the receiving circuitry 112 newly generates reflected wave data for one frame while the buffer memory 120 is storing therein the reflected wave data for the predetermined number of frames, the buffer memory 120 discards the reflected wave data for the oldest frame generated and stores therein the reflected wave data for the newly generated frame under control of the receiving circuitry 112. For example, the buffer memory 120 is implemented by a semiconductor memory device, such as a random access memory (RAM) and a flash memory.

The B-mode processing circuitry 130 reads out the reflected wave data from the buffer memory 120, applies various types of signal processing to the read-out reflected wave data, and outputs the reflected wave data subjected to the various types of signal processing to the image generation circuitry 150 as B-mode data. The B-mode processing circuitry 130 is implemented by, for example, a processor. The B-mode processing circuitry 130 is an example B-mode processing unit. The B-mode data is an example ultrasound signal.

For example, each time reflected wave data for one frame is newly stored in the buffer memory 120, the B-mode processing circuitry 130 reads out the reflected wave data for one frame newly stored in the buffer memory 120. The B-mode processing circuitry 130 then applies the various types of signal processing to the read-out reflected wave data for one frame to newly generate B-mode data for one frame. Each time the B-mode processing circuitry 130 generates B-mode data for one frame, the B-mode processing circuitry 130 outputs the newly generated B-mode data for one frame to the image generation circuitry 150. An example of the various types of signal processing executed by the B-mode processing circuitry 130 will be described below.

For example, the B-mode processing circuitry 130 performs quadrature detection on and applies envelope detection and logarithmic compression processing and the like to the reflected wave data read out from the buffer memory 120 to generate B-mode data in which the signal strength (amplitude strength) at each sample point is represented by brightness. The B-mode processing circuitry 130 then outputs the generated B-mode data to the image generation circuitry 150.

Here, using a function of the B-mode processing circuitry 130, the ultrasound diagnosis apparatus 1 can extract the third harmonic component from the reflected wave data (received signal) and generate B-mode image data based on the extracted third harmonic component. For example, the ultrasound diagnosis apparatus 1 uses the technique described in Japanese Patent Application Laid-open No. 2016-112400 to extract the third harmonic component from the reflected wave data. For example, the transmitting circuitry 111 causes the ultrasound probe 101 to execute three transmissions of ultrasound having phases (phases of the center frequency components contained in the ultrasound to be transmitted) differing by 120 degrees from each other. The receiving circuitry 112 generates three pieces of reflected wave data relating to a common reception scanning line on the basis of a plurality of reflected wave signals acquired through the three ultrasound transmissions. The B-mode processing circuitry 130 executes processing including phase rotation processing on two or more pieces of reflected wave data among the three pieces of reflected wave data to extract the second harmonic component, adds up the three pieces of reflected wave data, and extracts the third harmonic component. For example, the transmitting circuitry 111 causes the ultrasound probe 101 to transmit ultrasound in a first phase, to transmit ultrasound in a second phase in which the phase is advanced 120 degrees from the first phase, and to transmit ultrasound in a third phase in which the phase is advanced 240 degrees from the first phase. In other words, the transmitting circuitry 111 causes the ultrasound probe to transmit first ultrasound having a single center frequency component in the first phase, to transmit second ultrasound having a single center frequency component in the second phase in which the phase is substantially advanced 120 degrees from the first phase, and to transmit third ultrasound having a single center frequency component in the third phase in which the phase is substantially advanced 240 degrees from the first phase. Here, "substantially" indicates any of the following: (1) allowing for an error; (2) allowing for advancing of the phase in the negative direction (for example, including a case where the ultrasound probe 101 transmits the first ultrasound in the first phase, transmits the second ultrasound in a second phase in which the phase is delayed 120 degrees from the first phase, and transmits the third ultrasound having a phase delayed 240 degrees from the first phase); and (3) allowing phase rotation of N degrees and phase rotation of N+360 degrees to be considered the same (for example, allowing phase rotation of 120 degrees, phase rotation of 480 degrees, and phase rotation of –240 degrees).

Then, for example, the receiving circuitry 112 generates first reflected wave data corresponding to the ultrasound transmission in the first phase, second reflected wave data corresponding to the ultrasound transmission in the second phase, and third reflected wave data corresponding to the ultrasound transmission in the third phase. The B-mode processing circuitry 130 adds up the first reflected wave data, reflected wave data having a phase advanced 120 degrees from that of the second reflected wave data, and reflected wave data having a phase advanced 240 degrees from that of the third reflected wave data and extracts the second harmonic component. Furthermore, the B-mode processing circuitry 130 adds up the first reflected wave data, the second reflected wave data, and the third reflected wave data, and extracts the third harmonic component. In other words, the B-mode processing circuitry 130 adds up the first reflected wave data, the second reflected wave data, and the third reflected wave data in which the phases of the second harmonic components are substantially aligned and extracts the second harmonic component. Furthermore, the B-mode processing circuitry 130 adds up the first reflected wave data, the second reflected wave data, and the third reflected wave data in which the phases of the third harmonic components are substantially aligned and extracts the third harmonic component. Here, for example, "substantially aligned" indicates allowing for a slight error.

Here, the third harmonic component extracted by the B-mode processing circuitry 130 is reflected wave data used as input data described later, which will be described in detail later. The B-mode processing circuitry 130 then applies a trained model 170a described later to this input data to acquire reflected wave data in which effect of saturation is reduced. That is, the B-mode processing circuitry 130 extracts the third harmonic component in which effect of saturation is reduced from the input data. Note that the B-mode processing circuitry 130 may extract the third harmonic component by subtracting fourth reflected wave data acquired by transmitting ultrasound in a fourth phase in which the phase is reversed from the first phase, from the first reflected wave data acquired by transmitting ultrasound in the first phase. The third harmonic component extracted in this way may be used as input data described later. Alternatively, the third harmonic component may be extracted by applying a trained model 170a described later to the reflected wave data generated by the beam former 115.

The B-mode processing circuitry 130 uses the above-described method to extract the second harmonic component and the third harmonic component. It can be said that the B-mode processing circuitry 130 having the function to extract the second harmonic component and the third harmonic component is an example extracting unit.

The B-mode processing circuitry 130 then generates B-mode data based on the extracted second harmonic component and outputs the generated B-mode data to the image generation circuitry 150. The B-mode processing circuitry 130 also generates B-mode data based on the extracted third harmonic component and outputs the generated B-mode data to the image generation circuitry 150.

The Doppler processing circuitry 140 reads out the reflected wave data from the buffer memory 120, applies various types of signal processing to the read-out reflected wave data, and outputs the reflected wave data subjected to the various types of signal processing to the image generation circuitry 150 as Doppler data. The Doppler processing circuitry 140 is implemented by, for example, a processor. The Doppler processing circuitry 140 is an example Doppler processing unit.

For example, each time reflected wave data for one frame is newly stored in the buffer memory 120, the Doppler processing circuitry 140 reads out the reflected wave data for one frame newly stored in the buffer memory 120. The Doppler processing circuitry 140 then applies the various types of signal processing to the read-out reflected wave data for one frame to newly generate Doppler data for one frame. Each time the Doppler processing circuitry 140 generates Doppler data for one frame, the Doppler processing circuitry 140 outputs the newly generated Doppler data for one frame to the image generation circuitry 150. An example of the various types of signal processing executed by the Doppler processing circuitry 140 will be described below.

For example, the Doppler processing circuitry 140 performs frequency analysis on the reflected wave data read out from the buffer memory 120 to extract movement information of a moving object (such as a blood flow, tissues, and a contrast agent echo component) based on the Doppler effect from the reflected wave data and generates Doppler data indicating the extracted movement information. For example, the Doppler processing circuitry 140 extracts the average speed, average dispersion values, average power values, and the like at multiple points as the movement information of the moving object and generates the Doppler data indicating the extracted movement information of the moving object. The Doppler processing circuitry 140 outputs the generated Doppler data to the image generation circuitry 150.

The ultrasound diagnosis apparatus 1 can use the above-described function of the Doppler processing circuitry 140 to execute the color Doppler method, also referred to as color flow mapping (CFM). In color flow mapping, ultrasound is transmitted and received on a plurality of scanning lines a plurality of times. In color flow mapping, a moving target indicator (MTI) filter is applied to a data string in the same position to restrain a signal (clutter signal) derived from a stationary tissue or a slow-moving tissue and to extract a signal derived from a blood flow (blood flow signal) from the data string in the same position. In color flow mapping, blood flow information, such as the blood flow speed (average speed), blood flow dispersion (average dispersion value), and blood flow power (average power value), is estimated from the blood flow signal. The Doppler processing circuitry 140 outputs color Doppler data indicating the blood flow information estimated by color flow mapping to the image generation circuitry 150. Note that the color Doppler data is example Doppler data.

The B-mode processing circuitry 130 and the Doppler processing circuitry 140 can process both two-dimensional reflected wave data and three-dimensional reflected wave data.

The image generation circuitry 150 generates various pieces of ultrasound image data from the B-mode data, the second harmonic component, and the third harmonic component output from the B-mode processing circuitry 130 and the Doppler data output from the Doppler processing circuitry 140. The image generation circuitry 150 is implemented by a processor.

For example, the image generation circuitry 150 generates two-dimensional B-mode image data in which the intensity of the reflected wave is represented by brightness, from two-dimensional B-mode data generated by the B-mode processing circuitry 130. Furthermore, the image generation circuitry 150 generates two-dimensional Doppler image data or two-dimensional color image data in which the movement information or the blood flow information is visualized, from two-dimensional Doppler data or color Doppler data generated by the Doppler processing circuitry 140. Note that the two-dimensional Doppler image data in which the movement information is visualized and the two-dimensional color image data in which the blood flow information is visualized are speed image data, dispersion image data, power image data, or a combination of these pieces of image data.

Here, the image generation circuitry 150 typically converts (scan-converts) a scanning line signal string of ultrasound scanning into a scanning line signal string in a video format typified by television and the like and generates ultrasound image data for display. For example, the image generation circuitry 150 performs coordinate transformation on the data output from the B-mode processing circuitry 130 and the Doppler processing circuitry 140 in accordance with the mode of ultrasound scanning by the ultrasound probe 101 to generate ultrasound image data for display. The image generation circuitry 150 may also perform, for example, image processing (smoothing processing) regenerating an average value image of brightness using a plurality of image frames after scan conversion, image processing (edge enhancement processing) using a differential filter in an image, or the like, as various types of image processing other than the scan conversion. The image generation circuitry 150 may composite the ultrasound image data with textual information of various parameters, a scale, a body mark, and the like.

Furthermore, the image generation circuitry 150 performs coordinate transformation on three-dimensional B-mode data generated by the B-mode processing circuitry 130 to generate three-dimensional B-mode image data. The image generation circuitry 150 also performs coordinate transformation on three-dimensional Doppler data generated by the Doppler processing circuitry 140 to generate three-dimensional Doppler image data. That is, the image generation circuitry 150 generates the "three-dimensional B-mode image data and three-dimensional Doppler image data" as "three-dimensional ultrasound image data (volume data)". The image generation circuitry 150 then performs various types of rendering processing on the volume data to generate various pieces of two-dimensional image data to display the volume data on the display 103.

The rendering processing performed by the image generation circuitry 150 includes, for example, processing using multi planer reconstruction (MPR) to generate MPR image data from the volume data. The rendering processing performed by the image generation circuitry 150 includes, for example, volume rendering (VR) processing generating two-dimensional image data in which three-dimensional information is reflected. The image generation circuitry 150 is an example image generation unit.

The B-mode data and Doppler data are ultrasound image data before the scan conversion processing, and the data generated by the image generation circuitry 150 is ultrasound image data for display after the scan conversion processing. Note that the B-mode data and Doppler data are also referred to as raw data.

If receiving B-mode data based on the second harmonic component from the B-mode processing circuitry 130, the image generation circuitry 150 generates B-mode image data on the basis of the B-mode data based on the second harmonic component. Similarly, if receiving B-mode data based on the third harmonic component from the B-mode processing circuitry 130, the image generation circuitry 150 generates B-mode image data on the basis of the B-mode data based on the third harmonic component.

The image memory 160 is a memory storing therein various pieces of image data generated by the image generation circuitry 150. The image memory 160 also stores therein the data generated by the B-mode processing circuitry 130 and the Doppler processing circuitry 140. The B-mode data and Doppler data stored in the image memory 160 can be called by the operator after diagnosis, for example, and is turned into the ultrasound image data for display via the image generation circuitry 150. For example, the image memory 160 is implemented by a semiconductor memory device, such as a random access memory (RAM) and a flash memory, a hard disk, or an optical disk.

The storage circuitry 170 stores therein a control computer program for performing scanning (ultrasound transmission and reception), image processing, and display processing, diagnosis information (such as a patient ID and doctor's findings), and various pieces of data, such as diagnosis protocols and various body marks. The storage circuitry 170 is also used for storing data stored by the image memory 160 and the like as necessary. For example, the storage circuitry 170 is implemented by a semiconductor memory device, such as a flash memory, a hard disk, or an optical disk.

The storage circuitry 170 of this embodiment also stores a trained model 170a therein. The storage circuitry 170 may store a trained model 170a at the time of delivery of the ultrasound diagnosis apparatus 1 or may store a trained model 170a acquired from an external device or the like after delivery of the ultrasound diagnosis apparatus 1. The trained model 170a will be described later.

The control circuitry 180 controls the overall processing of the ultrasound diagnosis apparatus 1. In specific, the control circuitry 180 controls processing of the transmitting circuitry 111, the receiving circuitry 112, the B-mode processing circuitry 130, the Doppler processing circuitry 140, and the image generation circuitry 150 on the basis of various setting requests input by the operator via the input device 102 and various control computer programs and various pieces of data read from the storage circuitry 170. The control circuitry 180 also controls the display 103 so that an ultrasound image based on the ultrasound image data for display stored in the image memory 160 is displayed. For example, the control circuitry 180 controls the display 103 so that a B-mode image based on the B-mode image data or a color image based on the color image data is displayed. The control circuitry 180 also controls the display 103 so that a B-mode image with a color image superimposed thereon is displayed.

Furthermore, the control circuitry 180 generates a composite image by compositing a B-mode image based on the B-mode image data generated on the basis of the B-mode data based on the second harmonic component and a B-mode image based on the B-mode image data generated on the basis of the B-mode data based on the third harmonic component. The control circuitry 180 then controls the display 103 so that the generated composite image is displayed.

The control circuitry 180 is an example display control unit or control unit. The control circuitry 180 is implemented by, for example, a processor.

The control circuitry 180 also controls ultrasound scanning by controlling the ultrasound probe 101 via the transmitting/receiving circuitry 110.

Note that the term "processor" used in the description indicates, for example, circuitry, such as a central processing unit (CPU), a graphics processing unit (GPU), an application specific integrated circuit (ASIC), or a programmable logic device (such as a simple programmable logic device (SPLD), a complex programmable logic device (CPLD), or a field programmable gate array (FPGA)). The processor achieves the function by reading out the computer program stored in the storage circuitry 170 and executing the read-out computer program. Note that instead of storing the computer program in the storage circuitry 170, the computer program may be incorporated directly into the circuitry of the processor. In this case, the processor reads out and executes the computer program incorporated into the circuitry to achieve the function. Note that each processor of this embodiment is not limited to being configured as single circuitry for each processor and may be configured as a single processor by combining a plurality of pieces of independent circuitry to achieve the function. Furthermore, the plural pieces of circuitry (for example, the B-mode processing circuitry 130, the Doppler processing circuitry 140, the image generation circuitry 150, and the control circuitry 180) in FIG. 1 may be integrated into a single processor to achieve the function. That is, the B-mode processing circuitry 130, the Doppler processing circuitry 140, the image generation circuitry 150, and the control circuitry 180 may be integrated into a single piece of processing circuitry implemented by a processor. Note that the transmitting/receiving circuitry 110, the B-mode processing circuitry 130, the Doppler processing circuitry 140, the image generation circuitry 150, and the control circuitry 180 may be integrated into a single pieces of processing circuitry including a processor.

The overall configuration of the ultrasound diagnosis apparatus 1 of the first embodiment has been described. With the above-described configuration, the ultrasound diagnosis apparatus 1 executes processing described below so as to acquire an ultrasound signal in which effect of saturation is robustly reduced and degradation in image quality is restrained.

Figure 4:
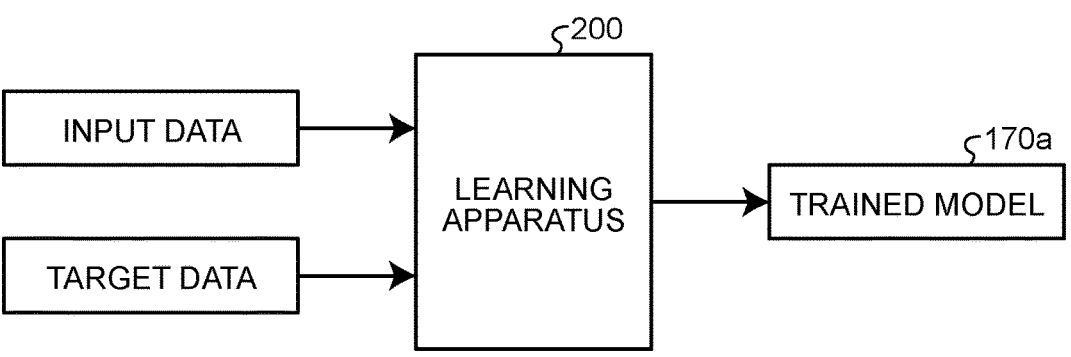
FIG. 4 is a diagram for describing an example trained model generation method according to the first embodiment.

FIG. 4 is a diagram for describing an example method of generating the trained model 170a according to the first embodiment. The trained model 170a is a trained machine learning model acquired by subjecting a machine learning model to machine learning in accordance with a model learning computer program on the basis of the input data and target data. The trained model 170a is generated by the learning apparatus 200.

The learning apparatus 200 includes a machine learning model, such as a convolution neural network (CNN). The learning apparatus 200 performs training (supervised training) based on the input data and target data relating to an ultrasonic examination of the same position (the same section, the same site) of a subject to generate the trained model 170a. The trained model 170a functions to output data corresponding to the target data (output data) when data corresponding to the input data is input at the time of inference. Note that the ultrasound diagnosis apparatus 1 may have a function similar to the function of the learning apparatus 200 and generate the trained model 170a instead of the learning apparatus 200.

A case where the machine learning model is a CNN will be described. In this case, in the learning apparatus 200, input data is input to the CNN being the machine learning model. The learning apparatus 200 applies the CNN to the input data to generate output data. The output data is then output from the CNN. In the learning apparatus 200, the output data is input to an evaluation function. In the learning apparatus 200, target data is also input to the evaluation function. The learning apparatus 200 evaluates the output data generated by the CNN on the basis of the input data and the target data with the evaluation function. The evaluation function, for example, compares the generated output data with the target data and modifies a coefficient (network parameter, such as weight and bias) of the CNN through error backpropagation. The evaluation by the evaluation function is fed back to the CNN. The learning apparatus 200 repeats such a series of supervised training based on the input data and target data acquired for the same position of the subject until, for example, a difference between the output data and the target data is equal to or smaller than a predetermined threshold. The learning apparatus 200 can output the trained machine learning model as a trained model.

For example, in the CNN, when input data and target data are provided, such a coefficient is generated that conversion into target data is performed from the characteristics of the input data. The greater the number of the input data and target data used for the machine learning, the better. For example, several thousands or more pieces of data are desirable.

Figure 5:
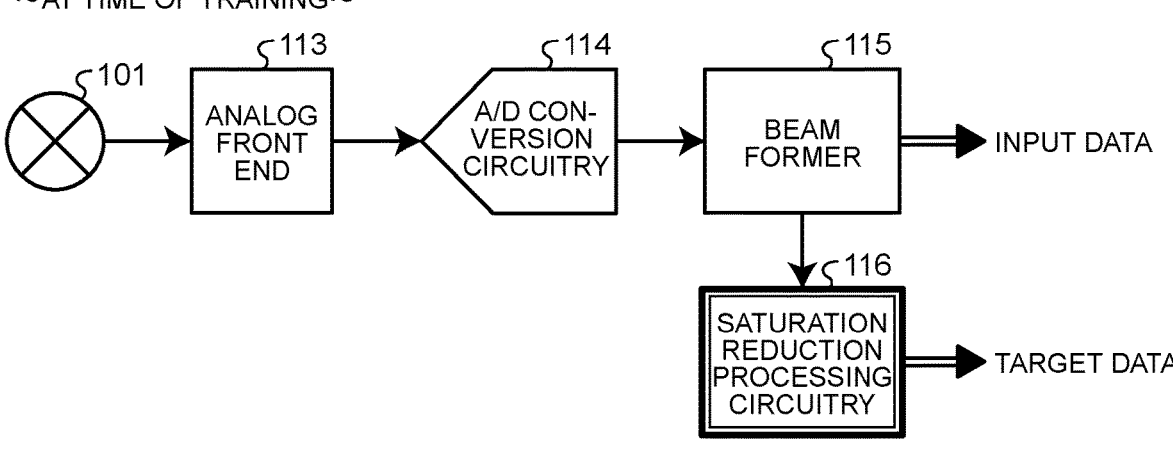
FIG. 5 is a diagram for describing an example input data and target data generation method according to the first embodiment.

A method of generating the input data and target data used for the machine learning at the learning apparatus 200 will be described with reference to FIG. 5. FIG. 5 is a diagram for describing an example input data and target data generation method according to the first embodiment. Note that the B-mode processing circuitry 130 connected to the subsequent stage of the beam former 115 is omitted in FIG. 5. As illustrated in FIG. 5, the reflected wave signal acquired by scanning a predetermined position of the subject P by the ultrasound probe 101 passes through the analog front end 113 and the A/D conversion circuitry 114 and is turned into reflected wave data by the beam former 115. Then, as described above, the B-mode processing circuitry 130 adds up the first reflected wave data, the second reflected wave data, and the third reflected wave data to acquire the third harmonic component. The third harmonic component (data after subjected to the phasing addition processing) as the reflected wave data is the input data. Furthermore, the saturation reduction processing circuitry 116 applies saturation reduction processing reducing effect of saturation on the reflected wave data being the input data.

Example saturation reduction processing executed by the saturation reduction processing circuitry 116 of the first embodiment will be described. For example, the saturation reduction processing circuitry 116 executes the saturation reduction processing applying a negative gain to a signal (portion) that is contained in the reflected wave data (input data) after the phasing addition processing and that is affected by saturation, thereby reducing the amplitude value of the signal affected by saturation.

In the reflected wave data subjected to the saturation reduction processing, effect of saturation is reduced in comparison with the reflected wave data as the input data. The reflected wave data subjected to this saturation reduction processing is the target data. That is, the saturation reduction processing circuitry 116 executes the saturation reduction processing to generate the target data.

The ultrasound diagnosis apparatus 1 then transmits the input data and target data generated in this way to the learning apparatus 200.

Note that the input data and target data are not limited to the above-described reflected wave data. For example, the reflected wave data output from the beam former 115 is turned into the B-mode data by the B-mode processing circuitry 130. This B-mode data may be the input data. For example, the input data is B-mode data based on the third harmonic component. In this case, the saturation reduction processing circuitry 116 applies the saturation reduction processing to the reflected wave data being the source of the input data. The reflected wave data subjected to the satura-tion reduction processing is turned into B-mode data by the B-mode processing circuitry 130. In this B-mode data based on the reflected wave data subjected to the saturation reduc-tion processing, effect of saturation is reduced in comparison with the B-mode data as the input data. The B-mode data based on the reflected wave data acquired by being subjected to this saturation reduction processing is the target data. For example, the reflected wave data output from the beam former 115 passes through the B-mode processing circuitry 130 and is turned into the B-mode image data by the image generation circuitry 150. This B-mode image data may be the input data. For example, the input data is B-mode image data based on the third harmonic component. In this case, the saturation reduction processing circuitry 116 applies the saturation reduction processing to the reflected wave data being the source of the input data. The reflected wave data subjected to the saturation reduction processing then passes through the B-mode processing circuitry 130 and is turned into B-mode image data by the image generation circuitry 150. In this B-mode image data based on the reflected wave data subjected to the saturation reduction processing, effect of saturation is reduced in comparison with the B-mode image data as the input data. The B-mode image data based on the reflected wave data acquired by being subjected to this saturation reduction processing is the target data.

The reflected wave data, B-mode data, and B-mode image data being the input data are examples of a first ultrasound signal containing a saturated signal. The reflected wave data, B-mode data, and B-mode image data being the target data are examples of a second ultrasound signal in which effect of saturation is reduced from the input data.

The learning apparatus 200 uses the input data and target data generated by the above-described method to train a learning model, thereby generating the trained model 170a. At this time, the learning apparatus 200 generates the trained model 170a for each site to be scanned. The ultrasound diagnosis apparatus 1 then acquires the trained model 170a generated for each site from the learning apparatus 200 and stores the acquired trained model 170a for each site in the storage circuitry 170.

Figure 6:
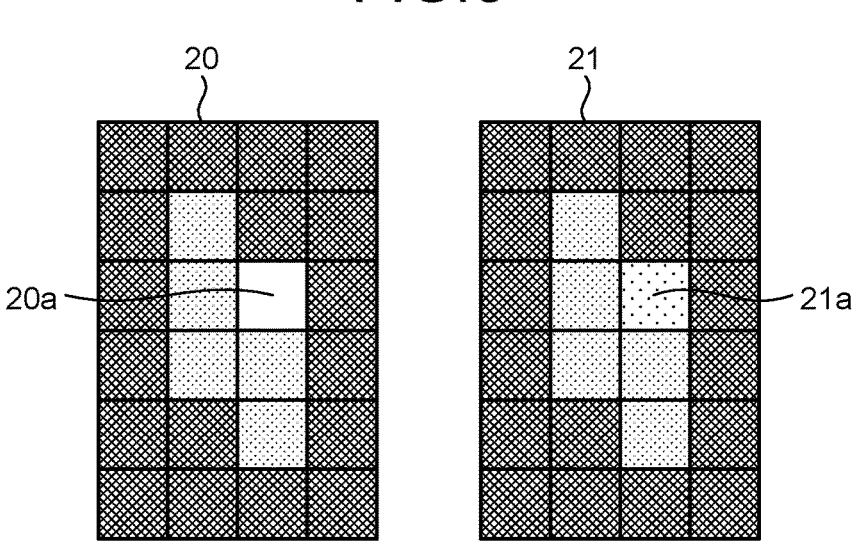
FIG. 6 is a diagram illustrating example input data and target data according to the first embodiment.

FIG. 6 is a diagram illustrating example input data and target data according to the first embodiment. An input data 20 contains a signal (saturated signal) 20a affected by saturation. On the other hand, reduction of a signal value of the saturated signal 20a in the input data 20 yields target data 21. The signal value of a signal 21a in the target data 21 is smaller than the signal value of the saturated signal 20a.

Figure 7:
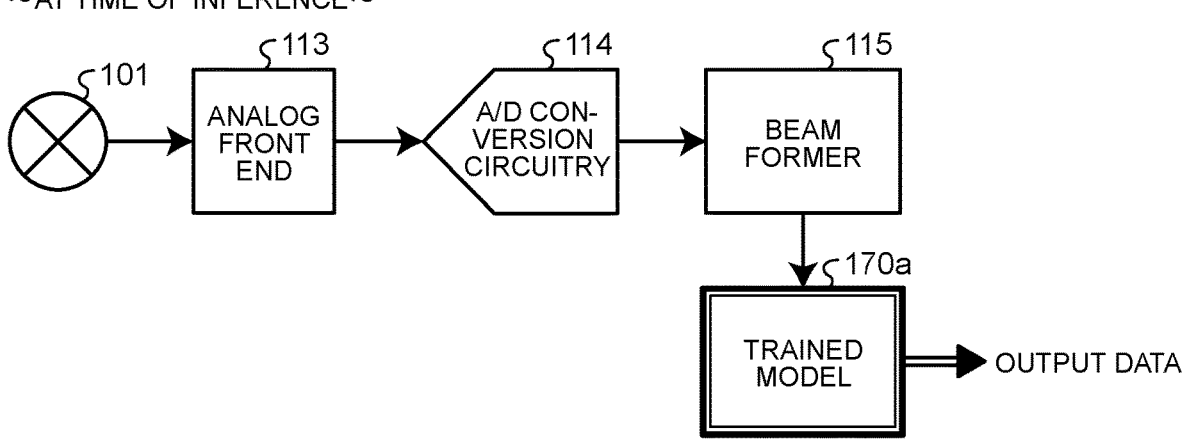
FIG. 7 is a diagram for describing example processing executed by the ultrasound diagnosis apparatus at the time of inference using a trained model, according to the first embodiment.

FIG. 7 is a diagram for describing example processing executed by the ultrasound diagnosis apparatus 1 at the time of inference using a trained model, according to the first embodiment. At the time of inference, the ultrasound diag-nosis apparatus 1 acquires a trained model 170a corresponding to a site to be scanned from the storage circuitry 170, uses the acquired trained model 170a to infer output data corresponding to input data, and outputs the inferred output data.

As illustrated in FIG. 7, for example, the ultrasound diagnosis apparatus 1 generates input data used at the time of inference in a manner similar to that for the input data used at the time of training. The input data used at the time of inference is data after subjected to the phasing addition processing and is an example third ultrasound signal con-taining a saturated signal.

When the input data used at the time of inference is input, the trained model 170a generates output data corresponding to the input data and outputs the generated output data. The output data is, for example, data in which effect of saturation is reduced in comparison with the input data used at the time of inference. That is, the output data is data in which the effect of saturation is reduced from the input data used at the time of inference. The output data is an example fourth ultrasound signal.

Here, the input data used at the time of inference is the reflected wave data, B-mode data, or B-mode image data as described above, and a case where the input data used at the time of inference is the reflected wave data will be described below.

In this case, the B-mode processing circuitry 130 acquires a trained model 170a corresponding to a site to be scanned among the trained models 170a for individual sites stored in the storage circuitry 170. The B-mode processing circuitry 130 then inputs the input data used at the time of inference to the acquired trained model 170a. For example, as described above, the B-mode processing circuitry 130 adds up three pieces of reflected wave data acquired through three ultrasound transmissions to extract the third harmonic com-ponent and inputs the extracted third harmonic component to the trained model 170a as the input data.

The B-mode processing circuitry 130 then acquires output data output from the trained model 170a. Here, the output data output from the trained model 170a is signal data containing the third harmonic component in which effect of saturation is reduced. Then, the B-mode processing circuitry 130 generates B-mode data on the basis of the output data, and the image generation circuitry 150 generates B-mode image data from the B-mode data as ultrasound image data.

Thus, the ultrasound diagnosis apparatus 1 of the first embodiment can acquire ultrasound image data in which effect of saturation is robustly reduced and degradation in image quality is restrained.

Note that if the input data used at the time of inference is the B-mode data, the B-mode processing circuitry 130 performs similar processing. In specific, the B-mode pro-cessing circuitry 130 inputs the B-mode data to the trained model 170a as the input data. The B-mode processing circuitry 130 then acquires output data output from the trained model 170a. Here, the output data output from the trained model 170a is B-mode data in which effect of saturation is reduced. The B-mode processing circuitry 130 then transmits the acquired output data (B-mode data in which the effect of saturation is reduced) to the image generation circuitry 150. The image generation circuitry 150 generates B-mode image data in which effect of saturation is reduced from the B-mode data in which the effect of saturation is reduced, as ultrasound image data.

If the input data used at the time of inference is the B-mode image data, the image generation circuitry 150 performs similar processing. In specific, the image genera-tion circuitry 150 inputs the B-mode image data to the trained model 170a as the input data. The image generation circuitry 150 then acquires output data output from the trained model 170a. Here, the output data output from the trained model 170a is B-mode image data in which effect of saturation is reduced. In this way, the image generation circuitry 150 uses the trained model 170a to generate the B-mode image data in which effect of saturation is reduced, from the input data.

Figure 8:
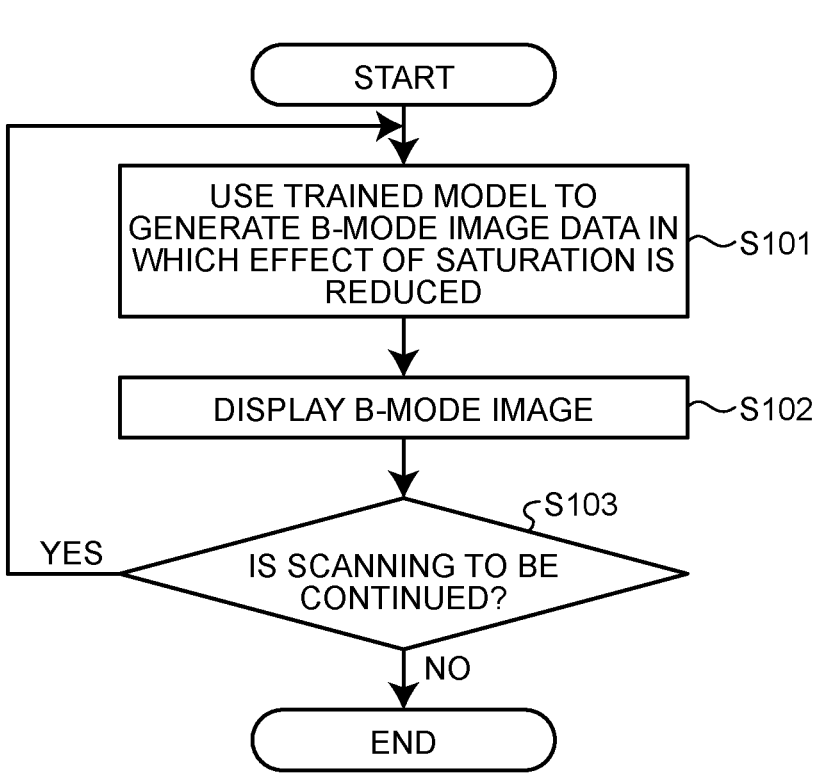
FIG. 8 is a flowchart illustrating an example flow of processing executed by the ultrasound diagnosis apparatus according to the first embodiment.

FIG. 8 is a flowchart illustrating an example flow of processing executed by the ultrasound diagnosis apparatus 1 according to the first embodiment. The processing illustrated in FIG. 8 is processing in which the ultrasound diagnosis apparatus 1 extracts the third harmonic component, generates B-mode image data based on the third harmonic component, and displays a B-mode image based on the generated B-mode image data.

As illustrated in FIG. 8, the ultrasound diagnosis apparatus 1 uses a trained model 170a to generate B-mode image data in which effect of saturation is robustly reduced and degradation in image quality is restrained (Step S101).

The ultrasound diagnosis apparatus 1 then displays a B-mode image based on the B-mode image data on the display 103 (Step S102).

The control circuitry 180 of the ultrasound diagnosis apparatus 1 then determines whether scanning is to be continued (Step S103). If scanning is to be continued (Yes at Step S103), the ultrasound diagnosis apparatus 1 returns to Step S101 and executes each process at Steps S101 to S103 again. Note that each process at Steps S101 to S103 is executed for each frame of the B-mode image displayed on the display 103. This enables the B-mode image to be displayed on the display 103 as a moving image.

If scanning is not to be continued (No at Step S103), the ultrasound diagnosis apparatus 1 ends the processing illustrated in FIG. 8.

Figure 9A:
FIG. 9A is a diagram illustrating an example B-mode image based on B-mode image data acquired from input data used at the time of training according to the first embodiment.
Figure 9B:
FIG. 9B is a diagram illustrating an example B-mode image based on B-mode image data acquired from target data used at the time of training according to the first embodiment.
Figure 9C:
FIG. 9C is a diagram illustrating an example B-mode image based on B-mode image data acquired from output data output from the trained model at the time of inference according to the first embodiment.

FIG. 9A is a diagram illustrating an example B-mode image based on B-mode image data acquired from input data used at the time of training according to the first embodiment. FIG. 9B is a diagram illustrating an example B-mode image based on B-mode image data acquired from target data used at the time of training according to the first embodiment. FIG. 9C is a diagram illustrating an example B-mode image based on B-mode image data acquired from output data output from the trained model 170a at the time of inference according to the first embodiment.

Portions (saturated regions) indicated by the arrows in a B-mode image 22 based on the input data used at the time of training, illustrated in FIG. 9A, are affected by saturation. Excessive contrast is provided to the saturated regions in comparison with the surroundings of the saturated regions.

In a B-mode image 23 based on the target data used at the time of training, illustrated in FIG. 9B, brightness of the regions corresponding to the saturated regions in FIG. 9A is decreased, resulting in reduction in a visual offense to the eye.

In a B-mode image 24 based on the output data output from the trained model 170a at the time of inference, illustrated in FIG. 9C, similar to the B-mode image 23, effect of saturation is reduced.

The ultrasound diagnosis apparatus 1 of the first embodiment has been described. As described above, the ultrasound diagnosis apparatus 1 can acquire ultrasound image data in which effect of saturation is robustly reduced and degradation in image quality is restrained.

Second Embodiment

Next, an ultrasound diagnosis apparatus 1 of a second embodiment will be described. In description of the ultrasound diagnosis apparatus 1 of the second embodiment, points different from the ultrasound diagnosis apparatus 1 of the first embodiment are mainly described, and description of constituents similar to those of the ultrasound diagnosis apparatus 1 of the first embodiment may be omitted.

Figure 10:
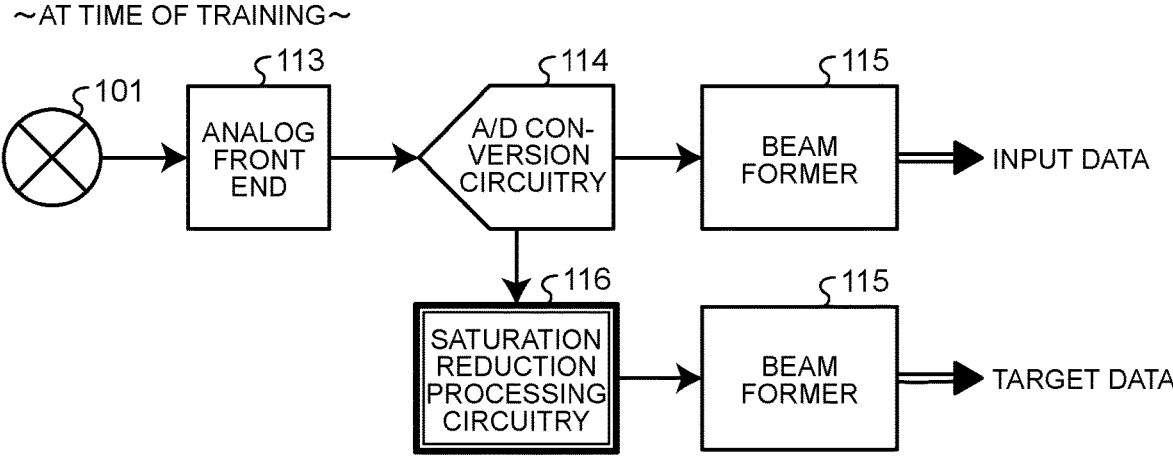
FIG. 10 is a diagram for describing an example input data and target data generation method according to a second embodiment.

A method of generating input data and target data used for machine learning at the learning apparatus 200 in the second embodiment will be described with reference to FIG. 10. FIG. 10 is a diagram for describing an example input data and target data generation method according to the second embodiment. Note that the B-mode processing circuitry 130 connected to the subsequent stage of the beam former 115 is omitted in FIG. 10.

As illustrated in FIG. 10, the method of generating the input data used at the time of training in the second embodiment is similar to the method of generating the input data used at the time of training in the first embodiment.

On the other hand, the method of generating the target data used at the time of training in the second embodiment differs from the method of generating the target data used at the time of training in the first embodiment. This point will be described specifically.

For example, as illustrated in FIG. 10, a reflected wave signal acquired by scanning a predetermined position of the subject P by the ultrasound probe 101 passes through the analog front end 113 and is turned into a digital signal by the A/D conversion circuitry 114. The saturation reduction processing circuitry 116 then applies saturation reduction processing reducing effect of saturation on this digital reflected wave signal. The reflected wave signal in which effect of saturation is reduced passes through the beam former 115 and the B-mode processing circuitry 130 and is subjected to processing similar to the processing acquiring the third harmonic component in the above-described first embodiment, thereby acquiring the third harmonic component. In the second embodiment, reflected wave data based on this third harmonic component, B-mode data based on the third harmonic component, or B-mode image data based on the third harmonic component is used as the target data. That is, the target data is acquired by reducing effect of saturation on the reflected wave signal after converted into a digital signal and before subjected to phasing addition processing.

Example saturation reduction processing executed by the saturation reduction processing circuitry 116 of the second embodiment will be described. For example, the saturation reduction processing circuitry 116 uses a technique similar to the technique described in Japanese Patent Application Laid-open No. 2017-55845 to reduce effect of saturation on the reflected wave signal. For example, the saturation reduction processing circuitry 116 determines whether the reflected wave signal is saturated for each channel. To provide description with a specific example, the saturation reduction processing circuitry 116 detects saturation using a state where the value of the reflected wave signal output from the A/D conversion circuitry 114 is at a positive upper or negative lower digital limit. Note that the saturation reduction processing circuitry 116 may determine that the reflected wave signal is saturated if the value of the reflected wave signal is equal to or greater than a predetermined threshold, and determine that the reflected wave signal is not saturated if the value of the reflected wave signal is smaller than the predetermined threshold. The saturation reduction processing circuitry 116 then multiplies the value of the reflected wave signal of a channel determined to be saturated by a coefficient smaller than 1 and outputs the reflected wave signal (reflected wave signal of the channel determined to be saturated) acquired as a result of the multiplication to the beam former 115. On the other hand, the saturation reduction processing circuitry 116 outputs the reflected wave signal of a channel determined not to be saturated to the beam former 115 as it is. Thus, the target data is acquired by determining whether the reflected wave signal is saturated for each channel and by adding weight to the reflected wave signal for each channel while using the coefficient for each channel in accordance with the determination result as the weight.

Furthermore, the saturation reduction processing circuitry 116 may apply another saturation reduction processing to the reflected wave signal. For example, the saturation reduction processing circuitry 116 determines whether the reflected wave signal is saturated for each channel. The saturation reduction processing circuitry 116 then estimates a value of the reflected wave signal of a channel determined to be saturated through interpolation processing using the value of the reflected wave signal of a channel determined not to be saturated. The saturation reduction processing circuitry 116 then replaces the value of the reflected wave signal of the channel determined to be saturated with the estimated reflected wave signal value. The saturation reduction processing circuitry 116 then outputs the value, after the replacement, of the reflected wave signal of the channel determined to be saturated, to the beam former 115. On the other hand, the saturation reduction processing circuitry 116 outputs the reflected wave signal of a channel determined not to be saturated to the beam former 115 as it is. Thus, the target data is acquired by determining whether the reflected wave signal is saturated for each channel and by replacing the value of the reflected wave signal of a channel determined to be saturated with a reflected wave signal value estimated using the value of the reflected wave signal of a channel determined not to be saturated.

In the reflected wave signal subjected to the saturation reduction processing, effect of saturation is reduced in comparison with the reflected wave signal that is not subjected to the saturation reduction processing. The target data based on the reflected wave signal subjected to such saturation reduction processing is an example second ultrasound signal.

The ultrasound diagnosis apparatus 1 then transmits the input data and target data generated in this way to the learning apparatus 200.

Figure 12:
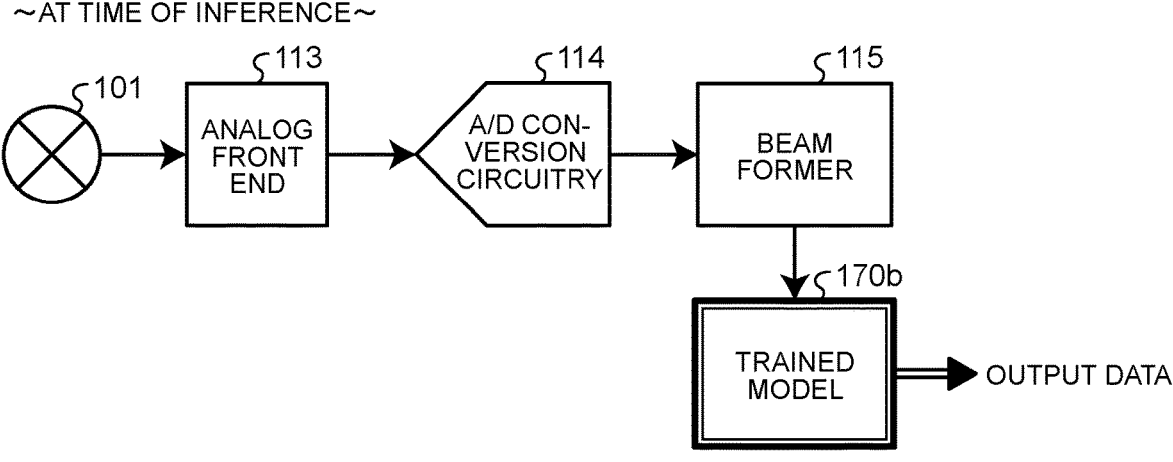
FIG. 12 is a diagram for describing example processing executed by an ultrasound diagnosis apparatus at the time of inference using a trained model, according to the second embodiment.

The learning apparatus 200 uses the input data and target data generated by the above-described method to train a training model, thereby generating a trained model 170b (see FIG. 12). At this time, the learning apparatus 200 generates the trained model 170b for each site to be scanned. The ultrasound diagnosis apparatus 1 then acquires the trained model 170b generated for each site from the learning apparatus 200 and stores the acquired trained model 170b for each site in the storage circuitry 170.

Figure 11:
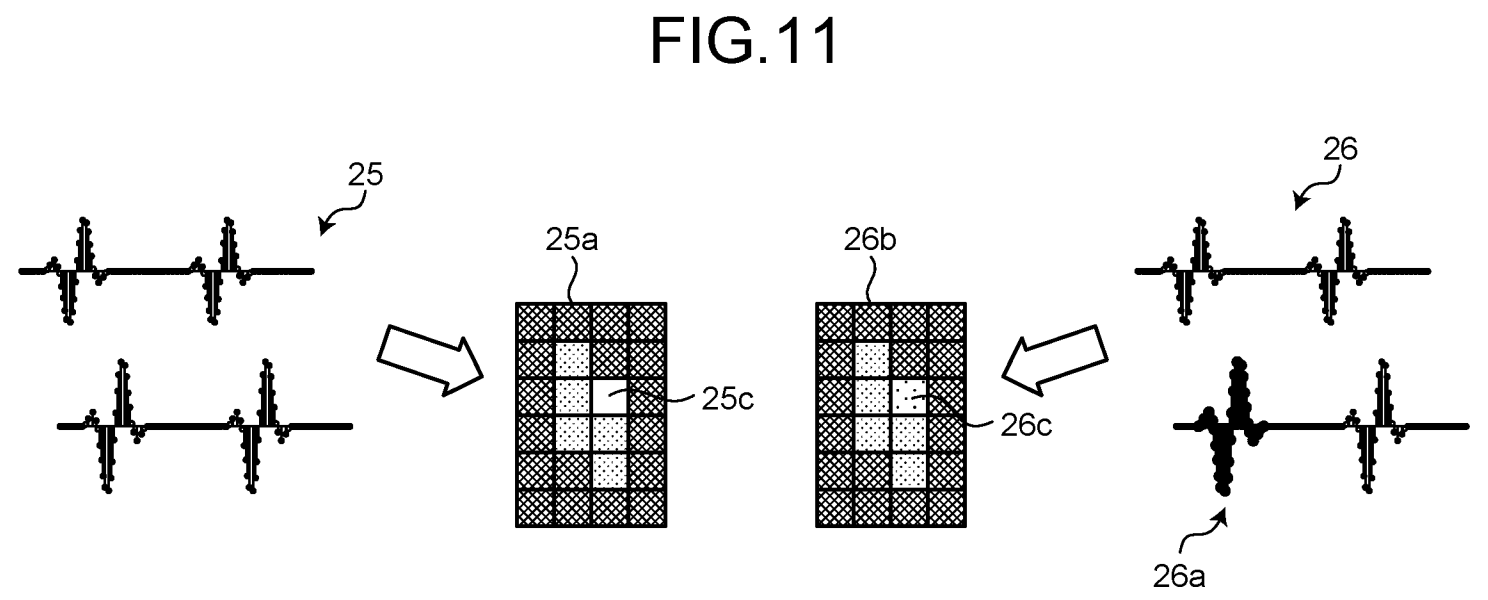

FIG. 11 is a diagram illustrating example input data and target data according to the second embodiment. Input data 25a contains a signal (saturated signal) 25c affected by saturation. A reflected wave signal 25 being the source of the input data 25a contains a saturated signal corresponding to the saturated signal 25c.

On the other hand, reduction of a signal value of the saturated signal in the reflected wave signal 25 yields target data 26b. In specific, reduction of the signal value of the saturated signal in the reflected wave signal 25 generates a reflected wave signal 26. In a signal 26a of the reflected wave signal 26 corresponding to the saturated signal of the reflected wave signal 25, effect of saturation is reduced.

Thus, the signal value of a signal 26c in the target data 26b is reduced from the signal value of the saturated signal 25c.

FIG. 12 is a diagram for describing example processing executed by the ultrasound diagnosis apparatus 1 at the time of inference of the trained model 170b, according to the second embodiment. At the time of inference, the ultrasound diagnosis apparatus 1 acquires a trained model 170b corresponding to a site to be scanned from the storage circuitry 170, uses the acquired trained model 170b to infer output data corresponding to input data, and outputs the inferred output data.

As illustrated in FIG. 12, for example, the ultrasound diagnosis apparatus 1 generates input data used at the time of inference in a manner similar to that for the input data used at the time of training.

When the input data used at the time of inference is input, the trained model 170b generates output data corresponding to the input data and outputs the generated output data. The output data is, for example, data in which effect of saturation is reduced in comparison with the input data used at the time of inference. That is, the output data is data in which the effect of saturation is reduced from the input data used at the time of inference. The output data is an example fourth ultrasound signal.

At the time of inference, the ultrasound diagnosis apparatus 1 of the second embodiment executes processing similar to the processing executed by the ultrasound diagnosis apparatus 1 of the first embodiment.

Thus, similar to the first embodiment, the ultrasound diagnosis apparatus 1 of the second embodiment can acquire ultrasound image data in which effect of saturation is robustly reduced and degradation in image quality is retrained.

Third Embodiment

Next, an ultrasound diagnosis apparatus 1 of a third embodiment will be described. In description of the ultrasound diagnosis apparatus 1 of the third embodiment, points different from the ultrasound diagnosis apparatus 1 of each of the above-described embodiments are mainly described, and description of constituents similar to those of the ultrasound diagnosis apparatus 1 of each of the above-described embodiments may be omitted.

Figure 13:
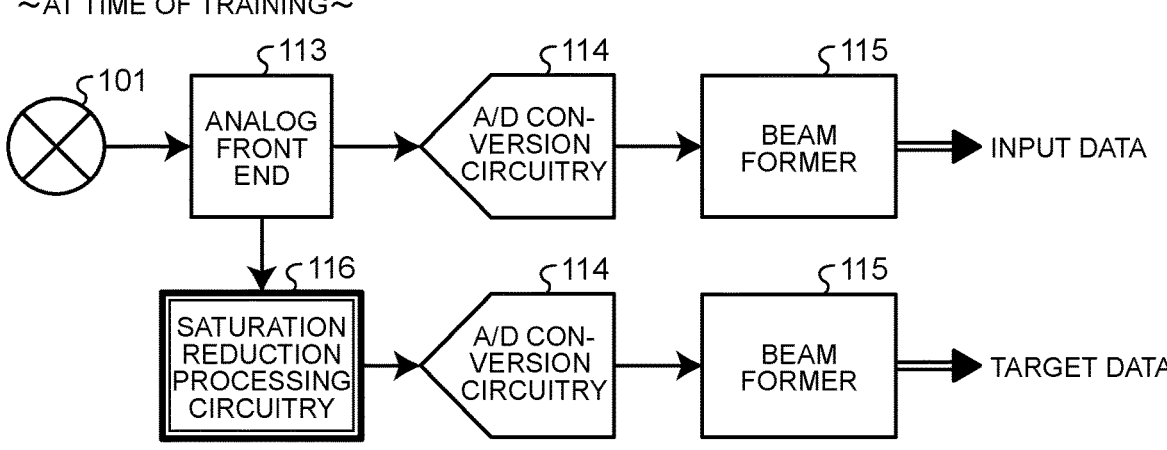
FIG. 13 is a diagram for describing an example input data and target data generation method according to a third embodiment.

A method of generating input data and target data used for machine learning at the learning apparatus 200 in the third embodiment will be described with reference to FIG. 13. FIG. 13 is a diagram for describing an example input data and target data generation method according to the third embodiment.

As illustrated in FIG. 13, the method of generating the input data used at the time of training in the third embodiment is similar to the method of generating the input data used at the time of training in the first embodiment.

On the other hand, the method of generating the target data used at the time of training in the third embodiment differs from the method of generating the target data used at the time of training in the first embodiment. This point will be described specifically.

For example, as illustrated in FIG. 13, a reflected wave signal acquired by scanning a predetermined position of the subject P by the ultrasound probe 101 is subjected to various types of analog processing by the analog front end 113. The saturation reduction processing circuitry 116 then applies saturation reduction processing reducing effect of saturation on the reflected wave signal being an analog signal subjected to the various types of analog processing.

Example saturation reduction processing executed by the saturation reduction processing circuitry 116 of the third embodiment will be described. For example, the saturation reduction processing circuitry 116 uses a known analog filter, such as a prefilter, to reduce effect of saturation on the reflected wave signal. For example, the saturation reduction processing circuitry 116 uses the prefilter to execute processing restraining a signal component (saturation-derived component) contained in the reflected wave signal and caused by saturation, as saturation reduction processing. The saturation reduction processing circuitry 116 then outputs the reflected wave signal subjected to the saturation reduction processing to the A/D conversion circuitry 114.

Furthermore, the saturation reduction processing circuitry 116 may apply another saturation reduction processing to the reflected wave signal. For example, the saturation reduction processing circuitry 116 determines whether the reflected wave signal is saturated. The saturation reduction processing circuitry 116 then applies an analog gain to the reflected wave signal determined to be saturated to reduce the amplitude value of the reflected wave signal. The saturation reduction processing circuitry 116 then outputs the reflected wave signal applied with the analog gain to the A/D conversion circuitry 114. On the other hand, the saturation reduction processing circuitry 116 outputs the reflected wave signal determined not to be saturated to the A/D conversion circuitry 114 as it is.

To the A/D conversion circuitry 114, the reflected wave signal output from the saturation reduction processing circuitry 116 is input. The A/D conversion circuitry 114 converts the input reflected wave signal into a digital signal and outputs the digital reflected wave signal in which effect of saturation is reduced, to the beam former 115.

The digital reflected wave signal in which effect of saturation is reduced then passes through the beam former 115 and the B-mode processing circuitry 130 and is subjected to processing similar to the processing acquiring the third harmonic component in the above-described first embodiment, thereby acquiring the third harmonic component. In the third embodiment, reflected wave data based on this third harmonic component, B-mode data based on the third harmonic component, or B-mode image data based on the third harmonic component is used as the target data.

This target data is an example second ultrasound signal. In this way, the target data is data after conversion of the reflected wave signal being an analog signal subjected to the saturation reduction processing reducing effect of saturation, into a digital signal. Furthermore, the target data is data after conversion of the reflected wave signal subjected to the saturation reduction processing applying an analog gain in accordance with a result of the determination of saturation of the reflected wave signal, into a digital signal.

The ultrasound diagnosis apparatus 1 then transmits the input data and target data generated in this way to the learning apparatus 200.

Figure 15:
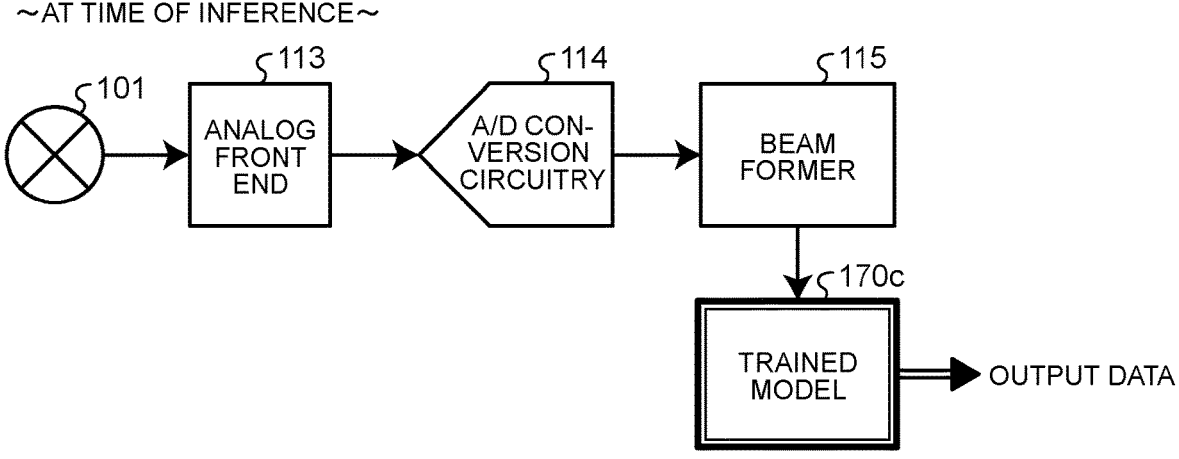
FIG. 15 is a diagram for describing example processing executed by an ultrasound diagnosis apparatus 1 at the time of inference using a trained model, according to the third embodiment.

The learning apparatus 200 uses the input data and target data generated by the above-described method to train a training model, thereby generating a trained model 170c (see FIG. 15). At this time, the learning apparatus 200 generates the trained model 170c for each site to be scanned. The ultrasound diagnosis apparatus 1 then acquires the trained model 170c generated for each site from the learning apparatus 200 and stores the acquired trained model 170c for each site in the storage circuitry 170.

Figure 14:
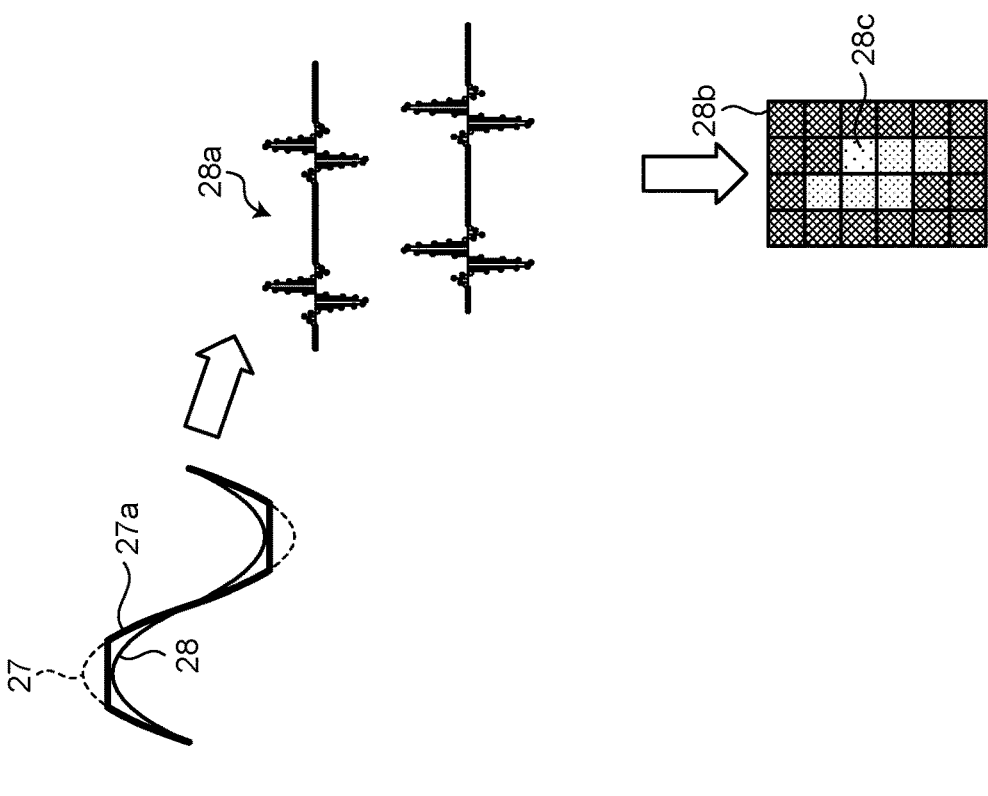
FIG. 14 is a diagram illustrating example input data and target data according to the third embodiment.
Figure 14:
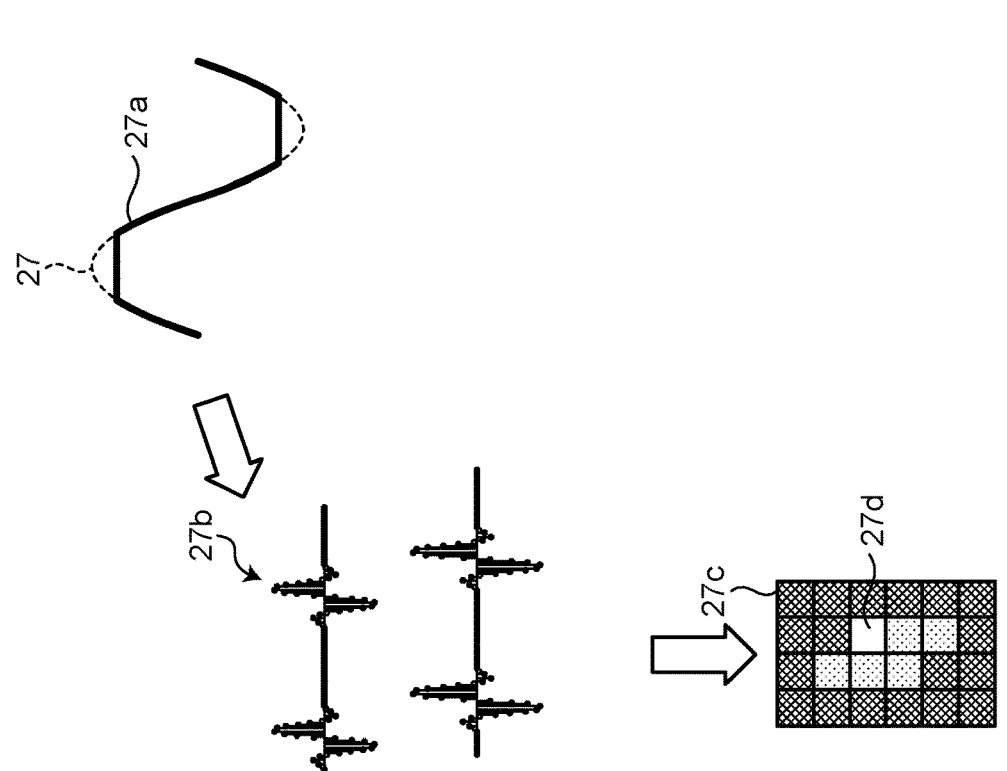

FIG. 14 is a diagram illustrating example input data and target data according to the third embodiment. As illustrated in FIG. 14, the analog front end 113 clips the amplitude of a reflected wave signal 27 equal to or greater than a certain value to the certain value to generate a reflected wave signal 27a. The A/D conversion circuitry 114 then converts the reflected wave signal 27a being an analog signal into a reflected wave signal 27b being a digital signal. The ultrasound diagnosis apparatus 1 then generates input data 27c from the reflected wave signal 27b.

The input data 27c contains a signal (saturated signal) 27d affected by saturation.

On the other hand, the saturation reduction processing circuitry 116 uses the prefilter to execute the saturation reduction processing restraining a signal component contained in the reflected wave signal 27a and caused by saturation. This generates a reflected wave signal 28 subjected to the saturation reduction processing. The A/D conversion circuitry 114 then converts the reflected wave signal 28 being an analog signal into a reflected wave signal 28a being a digital signal. The ultrasound diagnosis apparatus 1 then generates target data 28b from the reflected wave signal 28a. The signal value of a signal 28c in the target data 28b is reduced from the signal value of the signal 27d, corresponding to the signal 28c, in the input data 27c.

FIG. 15 is a diagram for describing example processing executed by the ultrasound diagnosis apparatus 1 at the time of inference of the trained model 170c, according to the third embodiment. At the time of inference, the ultrasound diagnosis apparatus 1 acquires a trained model 170c corresponding to a site to be scanned from the storage circuitry 170, uses the acquired trained model 170c to infer output data corresponding to input data, and outputs the inferred output data.

As illustrated in FIG. 15, for example, the ultrasound diagnosis apparatus 1 generates input data used at the time of inference in a manner similar to that for the input data used at the time of training.

When the input data used at the time of inference is input, the trained model 170c generates output data corresponding to the input data and outputs the generated output data. The output data is, for example, data in which effect of saturation is reduced in comparison with the input data used at the time of inference. That is, the output data is data in which the effect of saturation is reduced from the input data used at the time of inference. The output data is an example fourth ultrasound signal.

At the time of inference, the ultrasound diagnosis apparatus 1 of the third embodiment executes processing similar to the processing executed by the ultrasound diagnosis apparatus 1 of the first embodiment.

Thus, similar to the first embodiment and the like, the ultrasound diagnosis apparatus 1 of the third embodiment can acquire ultrasound image data in which effect of saturation is robustly reduced and degradation in image quality is retrained.

Fourth Embodiment

Next, an ultrasound diagnosis apparatus 1 of a fourth embodiment will be described. In description of the ultrasound diagnosis apparatus 1 of the fourth embodiment, points different from the ultrasound diagnosis apparatus 1 of each of the above-described embodiments are mainly described, and description of constituents similar to those of the ultrasound diagnosis apparatus 1 of each of the above-described embodiments may be omitted.

A method of generating input data and target data used for machine learning at the learning apparatus 200 in the fourth embodiment will be described with reference to FIG. 16.

Figure 16:
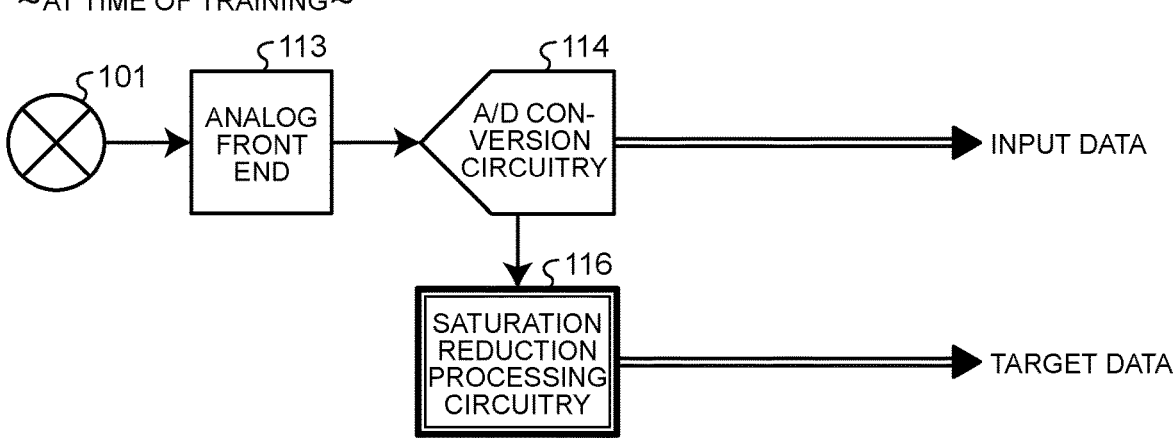
FIG. 16 is a diagram for describing an example input data and target data generation method according to a fourth embodiment.

FIG. 16 is a diagram for describing an example input data and target data generation method according to the fourth embodiment.

As illustrated in FIG. 16, a reflected wave signal acquired by scanning a predetermined position of the subject P by the ultrasound probe 101 passes through the analog front end 113 and is converted into a digital signal by the A/D conversion circuitry 114. A reflected wave signal of this digital signal is the input data. This reflected wave signal being the input data is an example first ultrasound signal containing a saturated signal. Furthermore, the reflected wave data being the input data is data after converted into a digital signal and before subjected to phasing addition processing.

Furthermore, the saturation reduction processing circuitry 116 applies saturation reduction processing reducing effect of saturation on the digital reflected wave signal being the input data. The saturation reduction processing circuitry 116 of the fourth embodiment applies saturation reduction processing similar to the saturation reduction processing executed by the saturation reduction processing circuitry 116 of the second embodiment, to the reflected wave signal.

In the reflected wave signal subjected to the saturation reduction processing, effect of saturation is reduced in comparison with the reflected wave signal as the input data. The reflected wave signal subjected to this saturation reduction processing is the target data. The reflected wave signal subjected to the saturation reduction processing is an example second ultrasound signal in which effect of saturation is reduced from the input data.

The ultrasound diagnosis apparatus 1 then transmits the input data and target data generated in this way to the learning apparatus 200.

Figure 18:
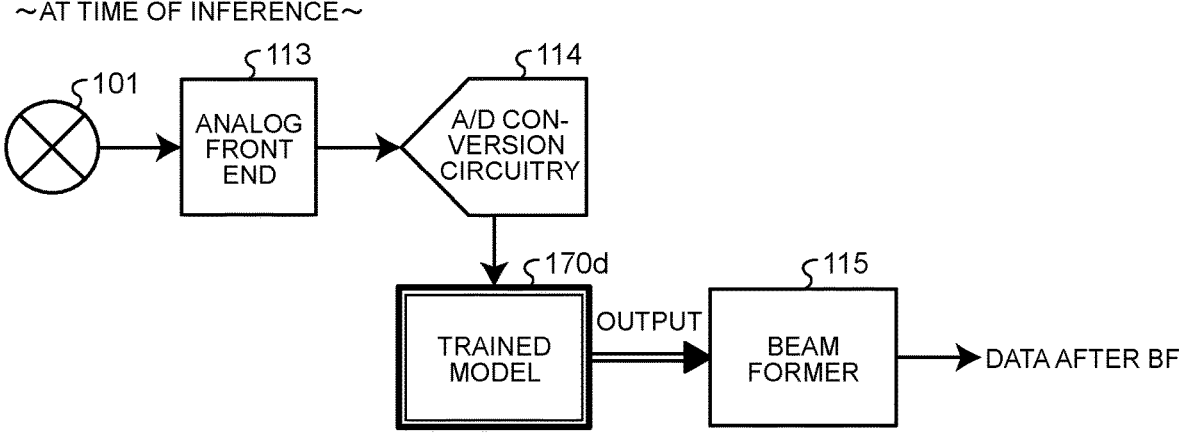
FIG. 18 is a diagram for describing example processing executed by an ultrasound diagnosis apparatus at the time of inference using a trained model, according to the fourth embodiment.

The learning apparatus 200 uses the input data and target data generated by the above-described method to train a training model, thereby generating a trained model 170*d* (see FIG. 18). At this time, the learning apparatus 200 generates the trained model 170*d* for each site to be scanned. The ultrasound diagnosis apparatus 1 then acquires the trained model 170*d* generated for each site from the learning apparatus 200 and stores the acquired trained model 170*d* for each site in the storage circuitry 170.

Figure 17:
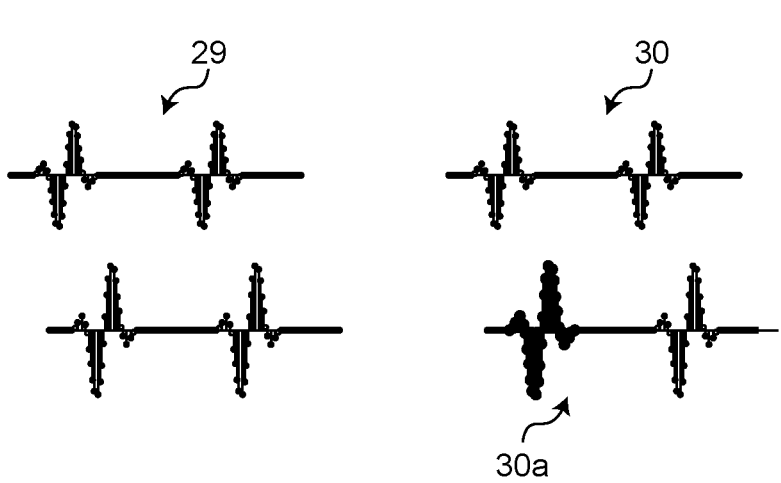
FIG. 17 is a diagram illustrating example input data and target data according to the forth embodiment.

FIG. 17 is a diagram illustrating example input data and target data according to the fourth embodiment. Input data 29 contains a saturated signal affected by saturation.

On the other hand, reduction of a signal value of the saturated signal in the input data 29 yields target data 30. In a signal 30*a* of the target data 30 corresponding to the saturated signal of the input data 29, effect of saturation is reduced. Thus, the signal value of the signal 30*a* of the target data 30 is reduced from the signal value of the saturated signal of the input data 29.

FIG. 18 is a diagram for describing example processing executed by the ultrasound diagnosis apparatus 1 at the time of inference of the trained model 170*d*, according to the fourth embodiment. At the time of inference, the ultrasound diagnosis apparatus 1 acquires a trained model 170*d* corresponding to a site to be scanned from the storage circuitry 170, uses the acquired trained model 170*d* to infer output data corresponding to input data, and outputs the inferred output data.

As illustrated in FIG. 18, for example, the ultrasound diagnosis apparatus 1 generates input data used at the time of inference in a manner similar to that for the input data used at the time of training. Here, the input data is generated for each channel. The input data used at the time of inference is an example third ultrasound signal containing a saturated signal. Furthermore, the input data is data after converted into a digital signal and before subjected to phasing addition processing.

When the input data used at the time of inference is input, the trained model 170*d* generates output data corresponding to the input data and outputs the generated output data. The output data is, for example, data in which effect of saturation is reduced in comparison with the input data used at the time of inference. That is, the output data is data in which the effect of saturation is reduced from the input data used at the time of inference. The output data is an example fourth ultrasound signal.

The A/D conversion circuitry 114 acquires a trained model 170*d* corresponding to a site to be scanned among the trained models 170*d* for individual sites stored in the storage circuitry 170. The A/D conversion circuitry 114 then inputs the input data used at the time of inference to the acquired trained model 170*d* for each channel.

The A/D conversion circuitry 114 acquires the output data output from the trained model 170*d* to generate the output data as a reflected wave signal for each channel. The A/D conversion circuitry 114 then outputs the generated reflected wave signal to the beam former 115. The beam former 115 applies phasing addition processing to the input reflected wave signal to generate reflected wave data.

When the ultrasound diagnosis apparatus 1 extracts the third harmonic component, the receiving circuitry 112 uses the above-described method using the trained model 170*d* to generate three pieces of reflected wave data relating to a common reception scanning line on the basis of a plurality of reflected wave signals acquired through three ultrasound transmissions. The B-mode processing circuitry 130 then adds up the three pieces of reflected wave data to extract the third harmonic component. That is, the B-mode processing circuitry 130 extracts the third harmonic component as a high-frequency component of a multiple order of 3 from the reflected wave data based on the output data output from the trained model 170*d*.

Here, the three pieces of reflected wave data used for extracting the third harmonic component are data in which effect of saturation is reduced. Thus, similar to the first embodiment and the like, the ultrasound diagnosis apparatus 1 of the fourth embodiment can acquire ultrasound image data in which effect of saturation is robustly reduced and degradation in image quality is restrained.

Fifth Embodiment

Next, an ultrasound diagnosis apparatus 1 of a fifth embodiment will be described. In description of the ultrasound diagnosis apparatus 1 of the fifth embodiment, points different from the ultrasound diagnosis apparatus 1 of each of the above-described embodiments are mainly described, and description of constituents similar to those of the ultrasound diagnosis apparatus 1 of each of the above-described embodiments may be omitted.

Figure 19:
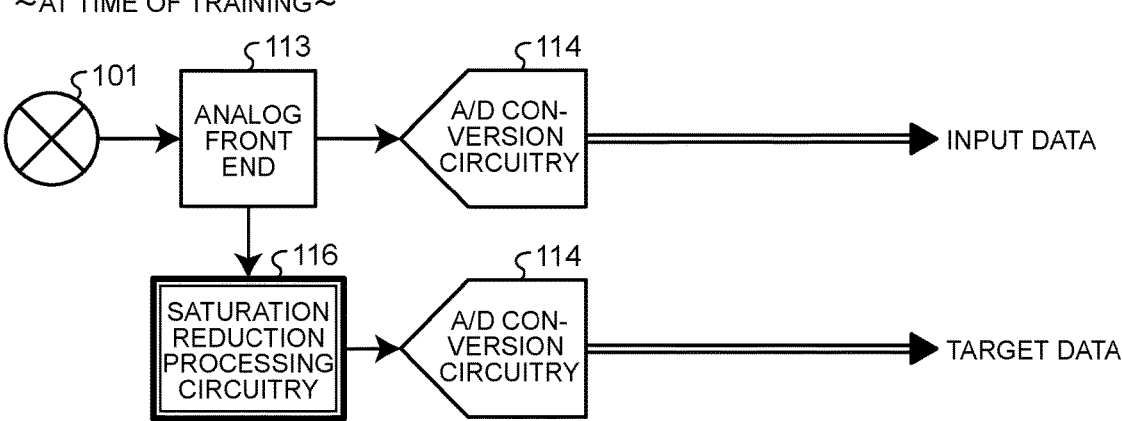
FIG. 19 is a diagram for describing an example input data and target data generation method according to a fifth embodiment.

A method of generating input data and target data used for machine learning at the learning apparatus 200 in the fifth embodiment will be described with reference to FIG. 19. FIG. 19 is a diagram for describing an example input data and target data generation method according to the fifth embodiment.

As illustrated in FIG. 19, the method of generating the input data used at the time of training in the fifth embodiment is similar to the method of generating the input data used at the time of training in the fourth embodiment. The method of generating the target data used at the time of training in the fifth embodiment will be described. For example, as illustrated in FIG. 19, a reflected wave signal acquired by scanning a predetermined position of the subject P by the ultrasound probe 101 is subjected to various types of analog processing by the analog front end 113. The saturation reduction processing circuitry 116 then applies saturation reduction processing reducing effect of saturation on the reflected wave signal being an analog signal subjected to the various types of analog processing.

Example saturation reduction processing executed by the saturation reduction processing circuitry 116 of the fifth embodiment will be described. For example, the saturation reduction processing circuitry 116 applies saturation reduction processing similar to the saturation reduction processing executed by the saturation reduction processing circuitry 116 of the third embodiment, to the reflected wave signal. The saturation reduction processing circuitry 116 then outputs the reflected wave signal subjected to the saturation reduction processing to the A/D conversion circuitry 114.

To the A/D conversion circuitry 114, the reflected wave signal output from the saturation reduction processing circuitry 116 is input. The A/D conversion circuitry 114 converts the input reflected wave signal into a digital signal.

In the reflected wave signal being the digital signal subjected to the saturation reduction processing, effect of saturation is reduced in comparison with the reflected wave signal as the input data. The reflected wave signal being the digital signal subjected to this saturation reduction processing is the target data. This reflected wave signal being the target data is an example second ultrasound signal. In this way, the target data is a reflected wave signal being an analog signal subjected to the saturation reduction processing reducing effect of saturation. Furthermore, the target data is a reflected wave signal subjected to the saturation reduction processing applying an analog gain in accordance with a result of the determination of saturation of the reflected wave signal.

The ultrasound diagnosis apparatus 1 then transmits the input data and target data generated in this way to the learning apparatus 200.

Figure 21:
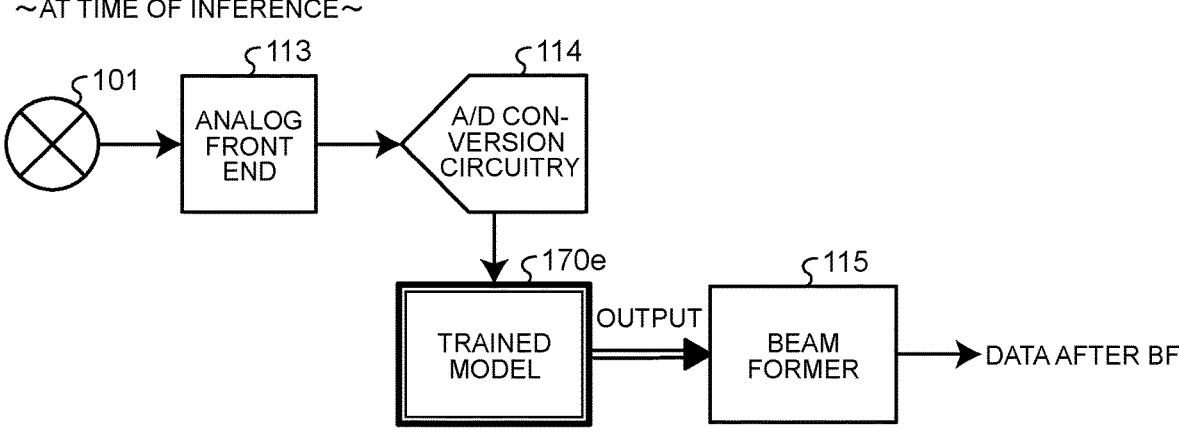
FIG. 21 is a diagram for describing example processing executed by an ultrasound diagnosis apparatus at the time of inference using a trained model, according to the fifth embodiment.

The learning apparatus 200 uses the input data and target data generated by the above-described method to train a training model, thereby generating a trained model 170e (see FIG. 21). At this time, the learning apparatus 200 generates the trained model 170e for each site to be scanned. The ultrasound diagnosis apparatus 1 then acquires the trained model 170e generated for each site from the learning apparatus 200 and stores the acquired trained model 170e for each site in the storage circuitry 170.

Figure 20:
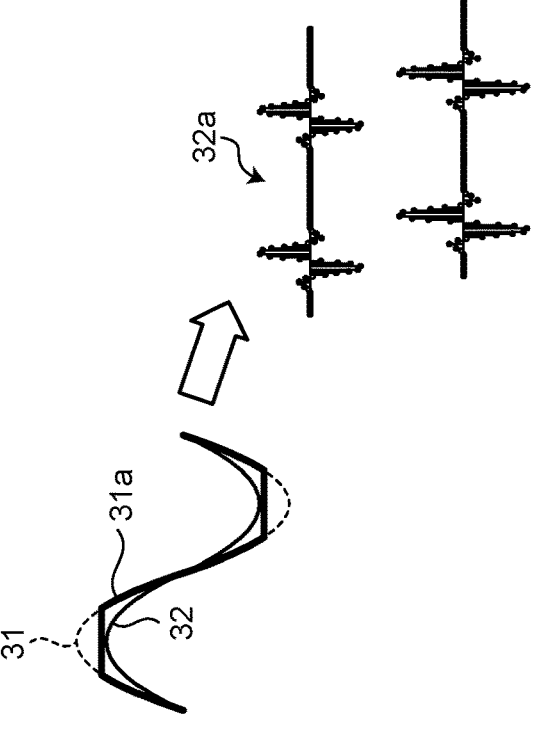
FIG. 20 is a diagram illustrating example input data and target data according to the fifth embodiment.
Figure 20:
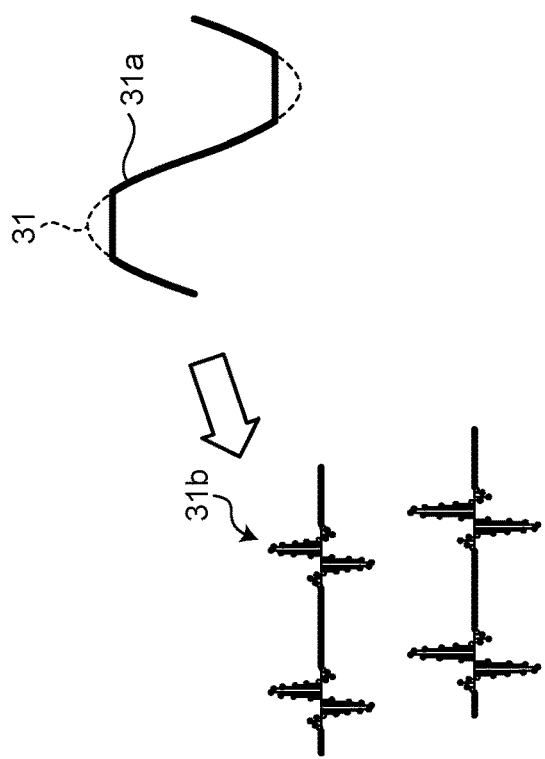

FIG. 20 is a diagram illustrating example input data and target data according to the fifth embodiment. As illustrated in FIG. 20, the analog front end 113 clips the amplitude of a reflected wave signal 31 equal to or greater than a certain value to the certain value to generate a reflected wave signal 31a. The A/D conversion circuitry 114 then converts the reflected wave signal 31a being an analog signal into a reflected wave signal 31b being a digital signal. This reflected wave signal 31b is the input data. The input data contains a saturated signal affected by saturation.

On the other hand, the saturation reduction processing circuitry 116 uses the prefilter to execute the saturation reduction processing restraining a signal component contained in the reflected wave signal 31a and caused by saturation. This generates a reflected wave signal 32 subjected to the saturation reduction processing. The A/D conversion circuitry 114 then converts the reflected wave signal 32 being an analog signal into a reflected wave signal 32a being a digital signal. This reflected wave signal 32a is the target data.

The signal value of a signal (signal corresponding to the saturated signal of the reflected wave signal 31b) of the reflected wave signal 32a being the target data is reduced from the signal value of the saturated signal of the reflected wave signal 31b being the input data.

FIG. 21 is a diagram for describing example processing executed by the ultrasound diagnosis apparatus 1 at the time of inference of the trained model 170e, according to the fifth embodiment. At the time of inference, the ultrasound diagnosis apparatus 1 acquires a trained model 170e corresponding to a site to be scanned from the storage circuitry 170, uses the acquired trained model 170e to infer output data corresponding to input data, and outputs the inferred output data.

As illustrated in FIG. 21, for example, the ultrasound diagnosis apparatus 1 generates input data used at the time of inference in a manner similar to that for the input data used at the time of training.

When the input data used at the time of inference is input, the trained model 170e generates output data corresponding to the input data and outputs the generated output data. The output data is, for example, data in which effect of saturation is reduced in comparison with the input data used at the time of inference. That is, the output data is data in which the effect of saturation is reduced from the input data used at the time of inference. The output data is an example fourth ultrasound signal.

The A/D conversion circuitry 114 acquires a trained model 170e corresponding to a site to be scanned among the trained models 170e for individual sites stored in the storage circuitry 170. The A/D conversion circuitry 114 then inputs the input data used at the time of inference to the acquired trained model 170e for each channel.

The A/D conversion circuitry 114 acquires the output data output from the trained model 170e to generate the output data as a reflected wave signal for each channel. The A/D conversion circuitry 114 then outputs the generated reflected wave signal to the beam former 115. The beam former 115 applies phasing addition processing to the input reflected wave signal to generate reflected wave data.

When the ultrasound diagnosis apparatus 1 extracts the third harmonic component, the receiving circuitry 112 uses the above-described method using the trained model 170e to generate three pieces of reflected wave data relating to a common reception scanning line on the basis of a plurality of reflected wave signals acquired through three ultrasound transmissions. The B-mode processing circuitry 130 then adds up the three pieces of reflected wave data to extract the third harmonic component. That is, the B-mode processing circuitry 130 extracts the third harmonic component as a high-frequency component of a multiple order of 3 from the reflected wave data based on the output data output from the trained model 170e.

Here, the three pieces of reflected wave data used for extracting the third harmonic component are data in which effect of saturation is reduced. Thus, similar to the first embodiment and the like, the ultrasound diagnosis apparatus 1 of the fifth embodiment can acquire ultrasound image data in which effect of saturation is robustly reduced and degradation in image quality is restrained.

MODIFICATION

Figure 22:
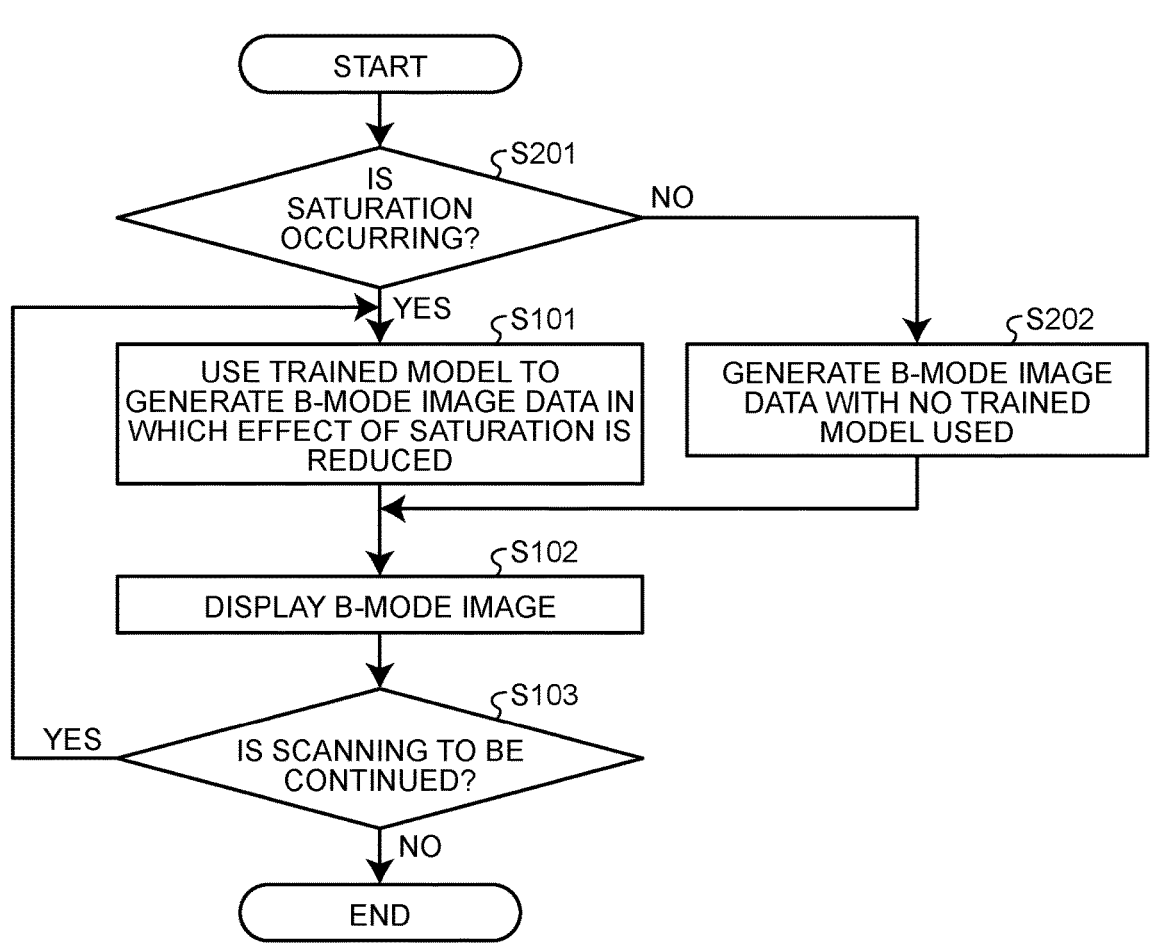
FIG. 22 is a flowchart illustrating an example flow of processing executed by an ultrasound diagnosis apparatus 1 according to a modification.

Next, an ultrasound diagnosis apparatus 1 of a modification will be described. FIG. 22 is a flowchart illustrating an example flow of processing executed by the ultrasound diagnosis apparatus 1 according to the modification. In each of the above-described embodiments, as illustrated in FIG. 22, when the third harmonic component is extracted, the control circuitry 180 of the ultrasound diagnosis apparatus 1 determines whether input data used at the time of inference is affected by saturation (Step S201). If it is determined that the input data used at the time of inference is affected by saturation (Yes at Step S201), the ultrasound diagnosis apparatus 1 may execute the above-described processes at Steps S101 to S103. For example, at Step S101, the ultrasound diagnosis apparatus 1 performs the above-described process using a trained model (trained model 170a, 170b, 170c, 170d, 170e) to extract the third harmonic component and generates B-mode image data based on the extracted third harmonic component.

On the other hand, if it is determined that the input data used at the time of inference is not affected by saturation (No at Step S201), the ultrasound diagnosis apparatus 1 extracts the third harmonic component with no trained model used and generates B-mode image data based on the extracted third harmonic component (Step S202). For example, at Step S202, three pieces of reflected wave data used when the B-mode processing circuitry 130 extracts the third harmonic component are reflected wave data generated by the beam former 115 with no trained model used. Then, the ultrasound diagnosis apparatus 1 proceeds to Step S102.

Note that the computer program executed by the processor is provided while being incorporated in a read only memory (ROM), the storage circuitry, or the like in advance. Note that the computer program may be provided as a file in a format installable or executable for these devices while being recorded in a computer-readable non-transitory storage medium, such as a compact disc (CD)-ROM, a flexible disk (FD), a CD-Recordable (R), and a digital versatile disc (DVD). Alternatively, the computer program may be provided or distributed by being stored in a computer connected to a network, such as the Internet, and downloaded via the network. For example, the computer program is composed of a module including each of the above-described processing functions. As actual hardware, a CPU reads out the computer program from the recording medium, such as a ROM, and executes the computer program to load and generate each module on a main storage device.

According to at least one embodiment or at least one modification described above, an ultrasound signal can be acquired in which effect of saturation is robustly reduced and degradation in image quality is restrained.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus comprising:
storage circuitry configured to store, in the storage circuitry, a trained model trained using a first ultrasound signal as input data and a second ultrasound signal as target data, the first ultrasound signal containing a saturated signal, effect of saturation being reduced in the second ultrasound signal from the first ultrasound signal; and processing circuitry configured to;
input, to the trained model, a third ultrasound signal containing a saturated signal;
acquire a fourth ultrasound signal output from the trained model to generate the fourth ultrasound signal, effect of saturation being reduced in the fourth ultrasound signal from the third ultrasound signal; and
generate the first ultrasound signal and the third ultrasound signal by executing analog signal processing including clamping processing retraining a signal value, equal to or greater than a certain value, of an ultrasound signal to the certain value, the ultrasound signal being acquired by transmitting and receiving ultrasound to and from a subject,
wherein the saturation occurs due to the clamping processing.

2. The ultrasound diagnosis apparatus according to claim 1, wherein the first ultrasound signal and the third ultrasound signal are configured to be data after subjected to phasing addition processing.

3. The ultrasound diagnosis apparatus according to claim 1, wherein the first ultrasound signal and the third ultrasound signal are configured to be data after converted into digital signals and data before subjected to phasing addition processing.

4. The ultrasound diagnosis apparatus according to claim 1, wherein the target data is configured to be the second ultrasound signal in which effect of saturation is reduced from the first ultrasound signal after subjected to phasing addition processing.

5. The ultrasound diagnosis apparatus according to claim 4, wherein the second ultrasound signal is configured to be generated by applying a negative gain to a signal contained in the first ultrasound signal and affected by saturation, thereby reducing an amplitude value of the signal affected by saturation.

6. The ultrasound diagnosis apparatus according to claim 1, wherein the second ultrasound signal being the target data is configured to be acquired by reducing effect of saturation on an ultrasound signal after converted into a digital signal and before subjected to phasing addition processing.

7. The ultrasound diagnosis apparatus according to claim 6, wherein the second ultrasound signal being the target data is configured to be acquired by determining whether the ultrasound signal is saturated for each channel and by adding weight to the ultrasound signal for each channel while using weight for each channel in accordance with a result of the determination.

8. The ultrasound diagnosis apparatus according to claim 6, wherein the second ultrasound signal being the target data is configured to be acquired by determining whether the ultrasound signal is saturated for each channel and by replacing a value of the ultrasound signal of a channel determined to be saturated with a value of an ultrasound signal estimated using a value of the ultrasound signal of a channel determined not to be saturated.

9. The ultrasound diagnosis apparatus according to claim 1, wherein the second ultrasound signal being the target data is configured to be data after conversion of an ultrasound signal into a digital signal, the ultrasound signal being an analog signal subjected to processing reducing effect of saturation.

10. The ultrasound diagnosis apparatus according to claim 9, wherein the processing reducing effect of saturation is configured to be processing using an analog filter to restrain a signal component caused by saturation.

11. The ultrasound diagnosis apparatus according to claim 9, wherein the second ultrasound signal being the target data is configured to be data after conversion of the ultrasound signal into a digital signal, the ultrasound signal being subjected to processing reducing effect of saturation by applying an analog gain in accordance with a result of determination of saturation of the ultrasound signal being an analog signal.

12. The ultrasound diagnosis apparatus according to claim 1, wherein the processing circuitry is further configured to extract an odd-order harmonic component from the fourth ultrasound signal and to generate ultrasound image data based on the extracted odd-order harmonic component.

13. The ultrasound diagnosis apparatus according to claim 1, wherein the processing circuitry is configured to determine whether the third ultrasound signal is affected by saturation, and, upon determination of the third ultrasound signal affected by saturation, to input the third ultrasound signal to the trained model and to acquire the fourth ultrasound signal output from the trained model to generate the fourth ultrasound signal.

14. An ultrasound signal generation method comprising:

inputting a third ultrasound signal containing a saturated signal to a trained model trained using a first ultrasound signal as input data and a second ultrasound signal as target data, the first ultrasound signal containing a saturated signal, effect of saturation being reduced in the second ultrasound signal from the first ultrasound signal;

acquiring a fourth ultrasound signal output from the trained model to generate the fourth ultrasound signal, effect of saturation being reduced in the fourth ultrasound signal from the third ultrasound signal; and generating the first ultrasound signal and the third ultrasound signal by executing analog signal processing including clamping processing retraining a signal value, equal to or greater than a certain value, of an ultrasound signal to the certain value, the ultrasound signal being acquired by transmitting and receiving ultrasound to and from a subject, wherein the saturation occurs due to the clamping processing.

* * * * *